(12) United States Patent
Sahli et al.

(10) Patent No.: US 10,035,807 B2
(45) Date of Patent: Jul. 31, 2018

(54) METHOD OF MANUFACTURING STEREOISOMERS OF BUPRENORPHINE AND ANALOGUES THEREOF

(71) Applicant: SIEGFRIED AG, Zofingen (CH)

(72) Inventors: Stefan Sahli, Zofingen (CH); Beat Theodor Weber, Zofingen (CH)

(73) Assignee: SIEGFRIED AG, Zofingen (CH)

( * ) Notice: Subject to any disclaimer, the term of this patent is extended or adjusted under 35 U.S.C. 154(b) by 0 days.

(21) Appl. No.: 15/557,311

(22) PCT Filed: Mar. 11, 2016

(86) PCT No.: PCT/EP2016/055249
§ 371 (c)(1),
(2) Date: Sep. 11, 2017

(87) PCT Pub. No.: WO2016/142506
PCT Pub. Date: Sep. 15, 2016

(65) Prior Publication Data
US 2018/0051032 A1 Feb. 22, 2018

(30) Foreign Application Priority Data
Mar. 11, 2015 (EP) ..................... 15158586

(51) Int. Cl.
*C07D 489/12* (2006.01)
(52) U.S. Cl.
CPC .................. *C07D 489/12* (2013.01)
(58) Field of Classification Search
CPC .................................................. C07D 489/12
USPC ......................................................... 546/39
See application file for complete search history.

(56) References Cited

U.S. PATENT DOCUMENTS 8,470,982 B2   6/2013   Knochel et al.
2009/0326235 A1  12/2009   Knochel et al.

FOREIGN PATENT DOCUMENTS

WO   2007026014 A1   3/2007

OTHER PUBLICATIONS

Kumar, V. et al.: Selectively promiscuous opioid ligands: Discovery of high afinity/low efficacy opioid ligands with substantial nociceptin opioid peptide receptor affinity. J. Med. Chem., vol. 57, pp. 4049-4057 as well as supporting information, p. S2, 2014.*
Marton, J. et al.: Studies on the synthesis of beta-thevinone derivatives. Tetrahedron, vol. 54, pp. 9143-9152, 1998.*
International Search Report for PCT/EP2016/055249 dated Jul. 7, 2016.

(Continued)

Primary Examiner — Charanjit Aulakh
(74) Attorney, Agent, or Firm — Millen White Zelano and Branigan, PC

(57) ABSTRACT

The present invention relates to a method of preparing a compound of Formula II-a' or Formula II-b', wherein $R^I$ represents hydrogen or a linear, branched and/or cyclic alkyl or alkenyl group having 1 to 10 carbon atoms; $R^{II}$ represents a linear, branched and/or cyclic alkyl or alkenyl group having 1 to 10 carbon atoms; $R^{III}$ represents hydrogen or a linear, branched and/or cyclic alkyl or alkenyl group having 1 to 10 carbon atoms or a linear, branched and/or cyclic alkoxy group having 1 to 10 carbon atoms; $R^{IV}$ represents hydrogen or a linear, branched and/or cyclic alkyl group having 1 to 10 carbon atoms or an optionally substituted aryl or alkylaryl group having 6 to 40 carbon atom or acetyl or silyl or a protective group; and $R^V$ represents hydrogen or a methyl group; wherein $R^I$ and $R^{II}$ are different from each other.

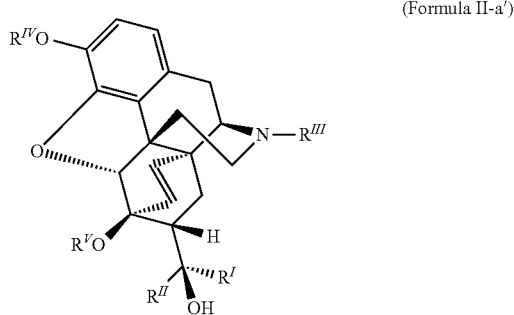

(Formula II-a')

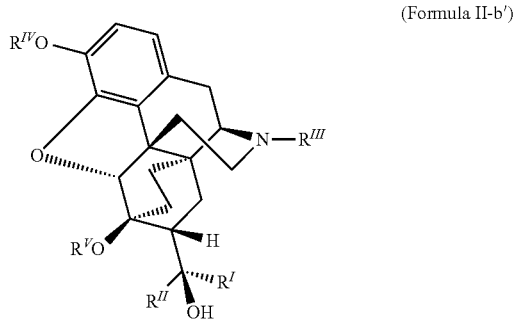

(Formula II-b')

15 Claims, No Drawings

(56) References Cited

OTHER PUBLICATIONS

Kumar, V. et al., "Selectively Promiscuous Opioid Ligands: Discovery of High Affinity/ Low Efficacy Opioid Ligands with Substantial Nociceptin Opioid Peptide Receptor Affinity," Journal of Medicinal Chemistry, May 22, 2014, vol. 57, No. 10, pp. 4049-4057.

Marton, J. et al., "Studies on the Synthesis of Beta-Thevinone Derivatives," Tetrahedron, 1998, vol. 54, pp. 9143-9152.

* cited by examiner

METHOD OF MANUFACTURING STEREOISOMERS OF BUPRENORPHINE AND ANALOGUES THEREOF

FIELD OF THE INVENTION

The present invention relates to a method of preparing a compound of Formula II-a' or Formula II-b', wherein $R^I$ represents hydrogen or a linear, branched and/or cyclic alkyl or alkenyl group having 1 to 10 carbon atoms; $R^{II}$ represents a linear, branched and/or cyclic alkyl or alkenyl group having 1 to 10 carbon atoms; $R^{III}$ represents hydrogen or a linear, branched and/or cyclic alkyl or alkenyl group having 1 to 10 carbon atoms or a linear, branched and/or cyclic alkoxy group having 1 to 10 carbon atoms; $R^{IV}$ represents hydrogen or a linear, branched and/or cyclic alkyl group having 1 to 10 carbon atoms or an optionally substituted aryl or alkylaryl group having 6 to 40 carbon atom or acetyl or silyl or a protective group; and $R^V$ represents hydrogen or a methyl group; wherein $R^I$ and $R^{II}$ are different from each other, as well as a mixture of isomers, particularly epimers, of the compound of Formula II-a or Formula II-b' obtained by the present method, wherein $R^I$ to $R^V$ have the same meaning as above.

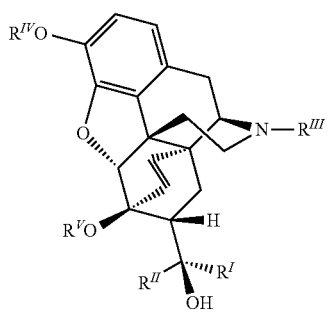

(Formula II-a')

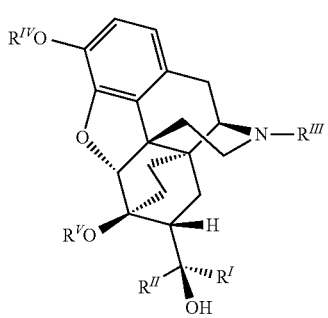

(Formula II-b')

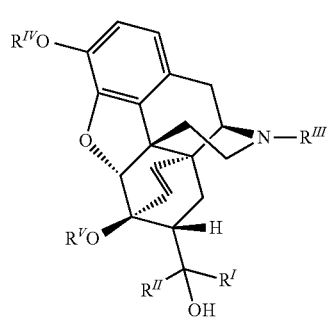

(Formula II-a)

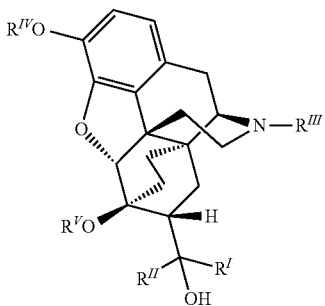

(Formula II-b)

The invention further relates to a method of preparing a compound of Formula II-a'-1 or Formula II-b'-1,

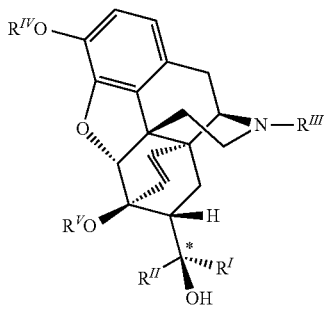

(Formula II-a'-1)

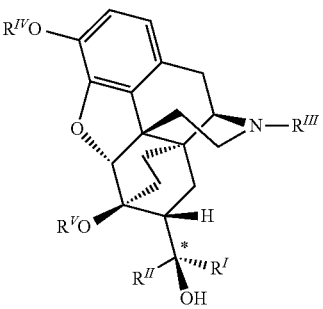

(Formula II-b'-1)

wherein $R^I$ represents a linear, branched and/or cyclic alkyl or alkenyl group having 2 to 10 carbon atoms;
$R^{II}$ represents methyl;
$R^{III}$ represents hydrogen or a linear, branched and/or cyclic alkyl or alkenyl group having 1 to 10 carbon atoms or a linear, branched and/or cyclic alkoxy group having 1 to 10 carbon atoms;
$R^{IV}$ represents hydrogen or a linear, branched and/or cyclic alkyl group having 1 to 10 carbon atoms or an optionally substituted aryl or alkylaryl group having 6 to 40 carbon atom or acetyl or silyl or a protective group; and
$R^V$ represents hydrogen or a methyl group;
and the stereochemistry at the position marked with * is S in case the carbon atom in $R^I$ next to the carbon atom marked with * is a carbon atom with a higher priority in the Cahn Ingold Prelog system as the thebaine-derived ring system, or the stereochemistry at the position marked with * is R in case the carbon atom next to the carbon atom marked with * in $R^I$ is a carbon atom with a lower priority in the Cahn Ingold Prelog system as the thebaine-derived ring system; or wherein $R^I$ represents a hydrogen or a methyl group;
$R^{II}$ represents a linear, branched and/or cyclic alkyl or alkenyl group having 2 to 10 carbon atoms;
$R^{III}$, $R^{IV}$ and $R^V$ have the same meanings as above;
and the stereochemistry at the position marked with * is S in case the carbon atom in $R^{II}$ next to the carbon atom marked with * is a carbon atom with a lower priority in the Cahn Ingold Prelog system as the thebaine-derived ring system, or the stereochemistry at the position marked with * is R in case the carbon atom next to the carbon atom marked with * in $R^{II}$ is a carbon atom with a higher priority in the Cahn Ingold Prelog system as the thebaine-derived ring system The invention further relates to a method of preparing stereoisomers, particularly epimers, of buprenorphine, etorphine, dihydroetorphine and analogues thereof and their salts.

STATE OF THE ART

Buprenorphine (cyclopropylmethyl-7-[(S)-3,3-dimethyl-2-hydroxybutan-2-yl]-6-methoxy-4,5-epoxy-6,14-ethanomorphinan-3-ol), generally administered in the form of its hydrochloride salt, is a potent semi-synthetic opiate analgesic, for the relief of moderate, chronic and acute pain, as well as in the therapy of opioid addiction. Since its approval it has been marketed as injectable solution, various types of tablets or patches. Buprenorphine can be administered as sole active ingredient or in combination with other substances such as naloxone, for example.

Recent studies by Greedy et al. (Greedy B. M., et al., J. Med. Chem. 2013, 56, 3207-2316) showed the differentiated potency of stereoisomers of buprenorphine and analogues thereof, for example as orvinols having mixed κ/μ [kappa/mu] opioid receptor agonist activity. In one aspect the capability to treat cocaine abuse has been shown.

Etorphine (5R,6R,7R,9R,13S,14R)-7-[(R)-2-Hydroxypentan-2-yl]-6-methoxy-17-methyl-4,5-epoxy-6,14-ethenomorphinan-3-ol) is a semi-synthetic opioid, having an analgesic potency of several thousand times higher that morphine. Etorphine is for veterinary use and is administered to immobilize large mammals as elephants.

18,19-dihydroetorphine, an analogue of buprenorphine, can be used as strong analgesic. Its clinical properties indicate administration as sublingual tablet or transdermal patches. Main application fields are the treatment of very intense pains and to treat addicts. Even though the potency of 18,19-dihydroetorphine is several thousand times higher than that of morphine, the observed side effects are mild.

Buprenorphine, etorphine, 18,19-dihydroetorphine, and diprenorphine can be shown by the following Formula 1 wherein $R^I$, $R^{II}$ and the carbon bond 18-19, which for simplicity sake is only shown as single bond in Formula 1, are defined as follows:

|  | R' | R" | Conformation at * | 18,19 bond |
|---|---|---|---|---|
| buprenorphine | methylcyclopropyl | tert-butyl | (S) | single |
| etorphine | methyl | n-propyl | (R) | double |
| 18,19-dihydroetorphine | methyl | n-propyl | (R) | single |
| diprenorphine | methylcyclopropyl | methyl | n.a. | single |

(Formula 1)

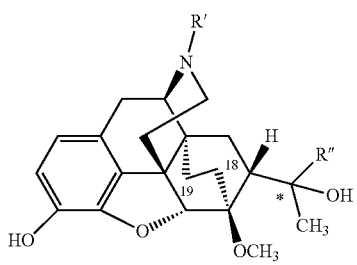

It is desirable to develop economic and ecologic methods to manufacture such substances and their pharmaceutically acceptable salts.

Several methods for synthesizing buprenorphine, its analogues and its stereoisomers from compounds isolated from the opium poppy or compounds derived therefrom are known. The most conventional ones use thebaine or oripavine, which are shown in Formula 2 below, wherein in case of thebaine R is methyl and in case of oripavine R is hydrogen, respectively, as starting material.

(Formula 2)

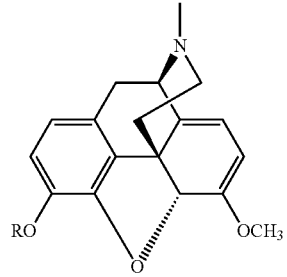

EP 1 439 179 (WO 2003/024972 and WO 2004/020220) discloses a classical route of synthesis from thebaine to buprenorphine and to analogues thereof. The synthetic route is a series of chemical reaction steps, including addition of a tert-butyl group by a Grignard reaction.

Greedy et al. (Greedy B. M., et al., J. Med. Chem. 2013, 56, 3207-2316) also disclose a process of manufacturing the target molecules. Drawback is the number of steps to get the substituents into the desired stereochemical conformation.

In EP 1 368 023 the use of buprenorphine and its stereoisomers in the treatment of urinary incontinence is described.

In WO 2013/042054 the use of buprenorphine and its stereoisomers in the treatment of acute suicidality is described.

The cited patent documents show the evident need of such substances, but no easy manufacturing process is presented. Thus there is a need of an efficient chemical process to manufacture such substances in a way the desired stereochemical conformation is obtained. In addition, there is in some cases the need of pharmaceutical acceptable salts to formulate stable pharmaceutical formulations.

Imamoto et al. (Imamoto T., Suigura Y., Takiyama N., Tetrahedron Letters, 1984 28(38), 4233-4236) already showed in 1984 mechanisms for the Grignard reactions using cerium instead of lithium or magnesium.

Routes of synthesis and different aspects of the Grignard reaction have been discussed in literature for a while. The use of Lanthanide (III) halides (La, Ce, and Nd), having the general formula LnCl3.2LiCl, which are soluble in tetrahydrofuran, has been presented by Krasovskiy et al. (Krasovskiy A., Kopp F., Knochel P., Angew. Chem. Int. Ed., 2006, 45, 497-500). Aim is an improvement of the Grignard reaction without further studying the stereochemistry of the substances.

An overview on state of the art applications of cerium chloride as agent in synthetic organic chemistry is given by Bartoli et al. (Bartoli G., Maractoni E., Marcolini M., Sambri L., Chem. Rev. 2010, 110, 6104-6413). Authors do not show if or how this technology could be used in the synthesis of stereo isomeric molecules.

Schuetz J. et al. (Schuetz J., Krassning R., Schmidhammer H., Wurst K., Lattanzi R., Heterocycles, 2001, 54, 989-998) present the addition of a Grignard reagent to thevinone without showing the ability to influence the stereochemistry.

Uff B. C., et al. (Uff B. C., Mallard A. S., Davis J. A., Henson R., magnetic resonance in chemistry, 1985, 26, 6 454-459) used up to about 5 mole equivalents of Grignard agent. Authors present valuable information on determining the stereochemical structure.

Marton J. et al. (Marton J., Szabó Z., Garadnay S., Miklós S., Makleit S., Tetrahedron, 1998, 54, 9143-9152) and (Marton J., Hosztafi S., Berényi S., Simon C., Makleit S., Monatsheft fuer die Chemie, 1994, 125, 1229-1239) used high amounts of Grignard reagent, i.e. about 6 mole equivalents have been used.

The proposed routes of synthesis still lack the ability of stereospecific Grignard reactions in the preparation of buprenorphine and analogues thereof, and the need of efficient chemical processes to manufacture such substances is still a requirement.

SUMMARY OF THE INVENTION

The current invention offers a novel method for converting side chains of morphine analogues leading to specific stereoisomers, particularly epimers, by a stereospecific organometallic reaction. The present inventors have found out that the presence of selected lanthanides as lanthanum, cerium or neodymium in the form of salts influence the stereochemical conformation of the resulting product.

In one aspect, the present invention relates to a method of preparing a compound of Formula II-a' or Formula II-b',

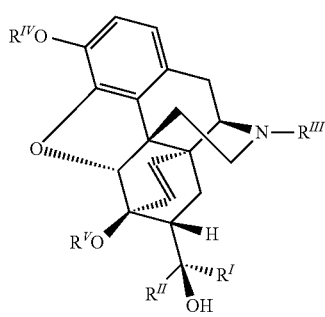

(Formula II-a')

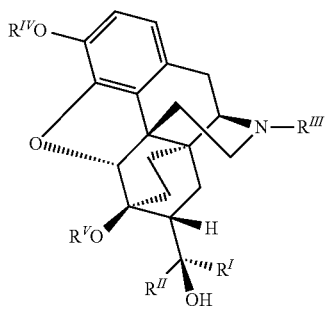

(Formula II-b')

wherein $R^I$ represents hydrogen or a linear, branched and/or cyclic alkyl or alkenyl group having 1 to 10 carbon atoms;

$R^{II}$ represents a linear, branched and/or cyclic alkyl or alkenyl group having 1 to 10 carbon atoms;

$R^{III}$ represents hydrogen or a linear, branched and/or cyclic alkyl or alkenyl group having 1 to 10 carbon atoms or a linear, branched and/or cyclic alkoxy group having 1 to 10 carbon atoms;

$R^{IV}$ represents hydrogen or a linear, branched and/or cyclic alkyl group having 1 to 10 carbon atoms or an optionally substituted aryl or alkylaryl group having 6 to 40 carbon atom or acetyl or silyl or a protective group; and $R^V$ represents hydrogen or a methyl group;

wherein $R^I$ and $R^{II}$ are different from each other, involving:

reacting a compound of Formula I-a or Formula I-b

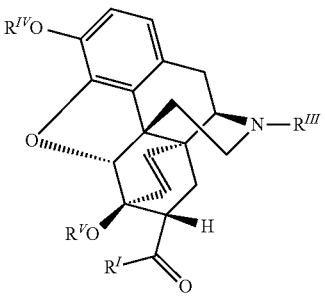

(Formula I-a)

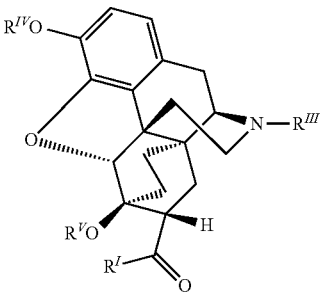

(Formula I-b)

wherein $R^I$, $R^{II}$, $R^{IV}$ and $R^V$ have the same meanings as above, with a reagent chosen from $R^{II}MgX$ and $R^{II}Li$, wherein $R^{II}$ has the same meaning as above and X is chosen from a halogen or pseudohalogen ion, in the presence of a compound of formula $LnY_3 \cdot nLiY$, wherein Ln is chosen from lanthanide ions, Y is chosen from halogenide or hydroxide, and n is 0, 1, 2 or 3, preferably n=0, 2.

In Formulas I-a, I-b, II-a' and II-b', $R^I$, $R^{II}$, $R^{III}$, $R^{IV}$, and $R^V$ can be the same or different, provided $R^I$ and $R^{II}$ are different.

Inventors found that stereochemistry at * in Formulas II-a'-1, II-b'-1, which correspond to Formulas II-a and II-b, respectively, apart from showing the stereo center at *, is substantially inversed when reacting in the presence of a Lanthanide (III) salt, or an adduct of the lanthanide (III) salt with a lithium salt, compared to the absence of such a salt. This means that the reaction proceeds according to the Felkin-Anh-model, particularly using a Grignard reagent, contrary to the mechanism described in J. Med. Chem, 2014, 57, pp. 4049-4057 for usual Grignard reactions.

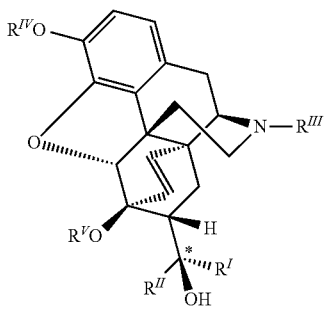

(Formula II-a'-1)

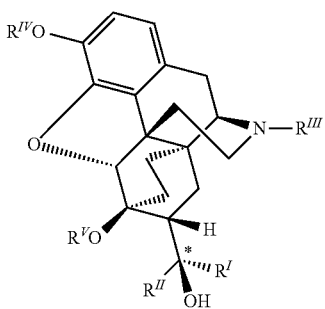

(Formula II-b'-1)

The inventive process gives good yield and in some cases allows a decrease in reaction steps as protection of critical groups can be avoided.

Thus, the present method also relates in an aspect to a method of preparing a compound of Formula II-a'-1 or Formula II-b'-1,

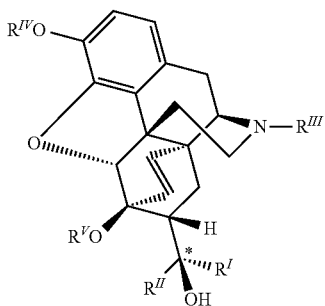

(Formula II-a'-1)

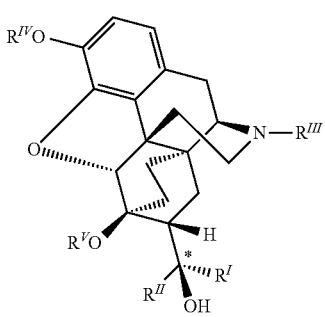

(Formula II-b'-1)

wherein $R^I$ represents a linear, branched and/or cyclic alkyl or alkenyl group having 2 to 10 carbon atoms;

$R^{II}$ represents methyl;

$R^{III}$ represents hydrogen or a linear, branched and/or cyclic alkyl or alkenyl group having 1 to 10 carbon atoms or a linear, branched and/or cyclic alkoxy group having 1 to 10 carbon atoms;

$R^{IV}$ represents hydrogen or a linear, branched and/or cyclic alkyl group having 1 to 10 carbon atoms or an optionally substituted aryl or alkylaryl group having 6 to 40 carbon atom or acetyl or silyl or a protective group; and $R^V$ represents hydrogen or a methyl group;

and the stereochemistry at the position marked with * is S in case the carbon atom in $R^I$ next to the carbon atom marked with * is a carbon atom with a higher priority in the Cahn Ingold Prelog system as the thebaine-derived ring system, or the stereochemistry at the position marked with * is R in case the carbon atom next to the carbon atom marked with * in $R^I$ is a carbon atom with a lower priority in the Cahn Ingold Prelog system as the thebaine-derived ring system; or wherein $R^I$ represents a hydrogen or a methyl group;

$R^{II}$ represents a linear, branched and/or cyclic alkyl or alkenyl group having 2 to 10 carbon atoms;

$R^{III}$, $R^{IV}$ and $R^V$ have the same meanings as above;

and the stereochemistry at the position marked with * is S in case the carbon atom in $R^{II}$ next to the carbon atom marked with * is a carbon atom with a lower priority in the Cahn Ingold Prelog system as the thebaine-derived ring system, or the stereochemistry at the position marked with * is R in case the carbon atom next to the carbon atom marked with * in $R^{II}$ is a carbon atom with a higher priority in the Cahn Ingold Prelog system as the thebaine-derived ring system, involving:

reacting a compound of Formula I-a or Formula I-b

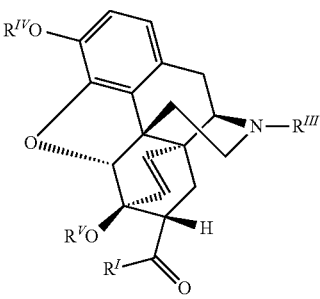

(Formula I-a)

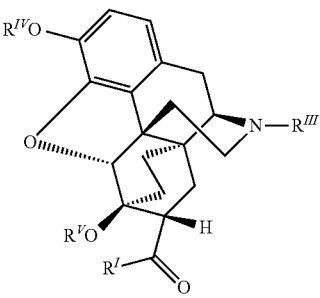

(Formula I-b)

wherein $R^I$, $R^{III}$, $R^{IV}$ and $R^V$ have the same meanings as above, with a reagent chosen from $R^{II}MgX$ and $R^{II}Li$, wherein $R^{II}$ has the same meaning as above and X is chosen from a halogen or pseudohalogen ion, in the presence of a compound of formula $LnY_3 \cdot nLiY$, wherein Ln is chosen from lanthanide ions and Y is chosen from halogenide or hydroxide ions, and n is 0, 1, 2 or 3, preferably n=0, 2.

According to a further aspect, the present invention relates to a mixture of isomers, particularly epimers, of the compound of Formula II-a or Formula II-b,

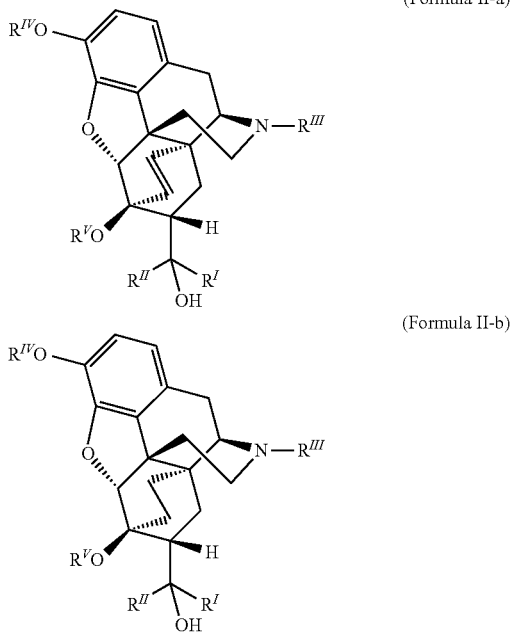

(Formula II-a)

(Formula II-b)

wherein $R^I$ represents hydrogen or a linear, branched and/or cyclic alkyl or alkenyl group having 1 to 10 carbon atoms; $R^{II}$ represents a linear, branched and/or cyclic alkyl or alkenyl group having 1 to 10 carbon atoms; $R^{III}$ represents hydrogen or a linear, branched and/or cyclic alkyl or alkenyl group having 1 to 10 carbon or a linear, branched and/or cyclic alkoxy group having 1 to 10 carbon atoms; $R^{IV}$ represents hydrogen or a linear, branched and/or cyclic alkyl group having 1 to 10 carbon atoms or an optionally substituted aryl or alkylaryl group having 6 to 40 carbon atom or acetyl or silyl or a protective group; and $R^V$ represents hydrogen or a methyl group;
wherein $R^I$ and $R^{II}$ are different from each other, which is obtained by the method of the present invention.

In Formulas II-a and II-b, $R^I$, $R^{II}$, $R^{III}$, $R^{IV}$, and $R^V$ can be the same or different, provided $R^I$ and $R^{II}$ are different.

Further embodiments are disclosed in the dependent claims and can be taken from the following description and examples, without being limited thereto.

DETAILED DESCRIPTION OF THE PRESENT INVENTION

All ranges disclosed herein are to be considered to be supplemented by the term "about", unless clearly defined to the contrary or otherwise clear from the context.

All numbers or percentages relating to amounts of a substance within this application are given in wt. %, unless clearly defined to the contrary or otherwise clear from the context.

In regard to this invention, a reference to a linear, branched and/or cyclic alkyl group refers to linear alkyl groups, branched alkyl groups, cyclic alkyl groups, cyclic alkyl groups with linear or branched alkyl groups attached, i.e. cycloalkylalkyl groups, and linear or branched alkyl groups with a cyclic alkyl group attached, i.e. alkylcycloalkyl groups, wherein the cyclic alkyl group in the alkylcycloalkyl groups can also have linear and/or branched alkyl groups attached.

In regard to this invention, a reference to a linear, branched and/or cyclic alkenyl group refers to linear alkenyl groups, branched alkenyl groups, cyclic alkenyl groups, cyclic alkyl groups with linear and/or branched alkenyl groups attached, i.e. cycloalkylalkenyl groups and alkenylcycloalkyl groups, and linear and/or branched alkyl groups with a cyclic alkenyl group attached, i.e. cycloalkenylalkyl groups and alkylcycloalkenyl groups, wherein the cyclic alkyl group in the alkenylcycloalkyl groups and cycloalkylalkenyl groups or the cyclic alkenyl group in the cycloalkenylalkyl groups and alkylcycloalkenyl groups can also have linear and/or branched alkyl and/or alkenyl groups attached.

For the sake of convenience the foregoing definitions for alkyl and alkenyl groups are summarized and referred to as alkyl or alkenyl groups.

A protective group with regard to the invention is not particularly limited as long as it protects the particular functional group in the present compound. For example, an alcohol protective group can be chosen form available and suitable groups, e.g. from carbon acid esters, alkyl, allyl, silyl ethers, acetyl, benzoyl, p-methoxybenzyl, benzyl, benzyloxymethyl, tetrahydrofuran, triphenylmethyl, tetrahydropyranyl, without being limited thereto, and can be e.g. an acetyl (Ac), a benzoyl (Bz), a Benzyl (Bn), a β-methoxyethoxymethyl ether (MEM), an alkoxymethyl group with 1 to 10 carbon atoms, e.g., without being limited thereto, a methoxymethyl ether (MOM), a silyl ether group, e.g. (trimethylsilyl)ethoxymethyl (SEM), or other known groups, whereas an amine protective group can e.g. be a tert-butyloxycarbonyl (BOC), carbobenzyloxy (Cbz), a p-methoxybenzyl carbonyl (Moz or MeOZ), a benzyl (Bn), a carbamate, a tosyl (Ts) or another sulfonyl group, or other known groups. A preferred protective group for an O-atom in a hydroxy or alkoxy functional group as e.g. in position 3, i.e. the group with $R^{IV}$, is, without being limited thereto, an acetyl or a silyl group.

A silyl group within the scope of the invention is a group comprising Si having attached up to three identical or different, optionally substituted, linear, branched, and/or cyclic alkyl, alkenyl and/or aromatic carbon groups having each 1 to 10 carbon atoms and/or hydrogen, particularly at least 2 carbon atoms for an alkenyl group and/or at least 3 carbon atoms for a cyclic alkyl or alkenyl group and/or at least 6 carbon atoms for an aromatic carbon group, wherein a substituent can be chosen from e.g. halogen.

The current invention offers a novel method for converting side chains of morphine analogues leading to specific stereoisomers, particularly epimers, by a stereospecific organometallic reaction. It has been found that the presence of lanthanides, especially selected lanthanides like lanthanum, cerium or neodymium, in the form of salts influence the conformation of the groups.

In one aspect, the present invention relates to a method of preparing a compound of Formula II-a' or Formula II-b', (Formula II-a')

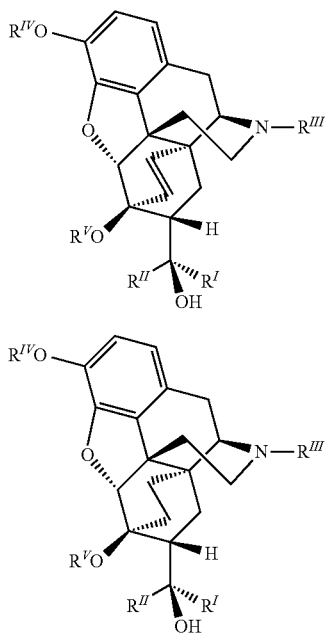

(Formula II-b')

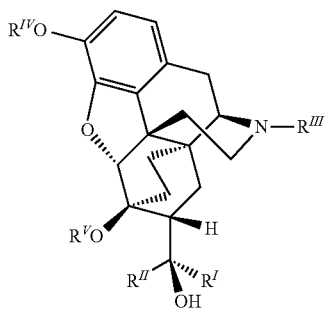

wherein $R^I$ represents hydrogen, a linear, branched and/or cyclic alkyl or alkenyl group having 1 to 10 carbon atoms, particularly at least 2 carbon atoms for an alkenyl group and/or at least 3 carbon atoms for a cyclic alkyl or alkenyl group;
$R^{II}$ represents a linear, branched and/or cyclic alkyl or alkenyl group having 1 to 10 carbon atoms, particularly at least 2 carbon atoms for an alkenyl group and/or at least 3 carbon atoms for a cyclic alkyl or alkenyl group;
$R^{III}$ represents hydrogen or a linear, branched and/or cyclic alkyl or alkenyl group having 1 to 10 carbon atoms, particularly at least 2 carbon atoms for an alkenyl group and/or at least 3 carbon atoms for a cyclic alkyl or alkenyl group, or a linear, branched and/or cyclic alkoxy group having 1 to 10 carbon atoms, particularly at least 3 carbon atoms for a cyclic alkoxy group;
$R^{IV}$ represents hydrogen or a linear, branched and/or cyclic alkyl group having 1 to 10 carbon atoms, particularly at least 3 carbon atoms for a cyclic alkyl group, or an optionally substituted aryl or alkylaryl group having 6 to 40 carbon atom or acetyl or silyl or a protective group; and
$R^V$ represents hydrogen or a methyl group;
wherein $R^I$ and $R^{II}$ are different from each other, involving: reacting a compound of Formula I-a or Formula I-b (Formula I-a)

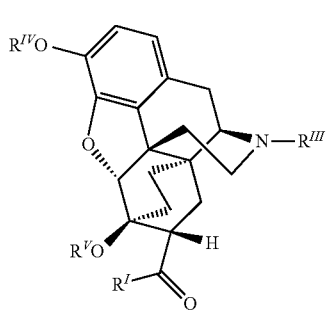

(Formula I-b)

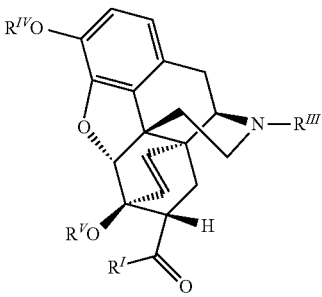

wherein $R^I$, $R^{III}$, $R^{IV}$ and $R^V$ have the same meanings as above,
with a reagent chosen from $R^{II}MgX$ and $R^{II}Li$, wherein $R^{II}$ has the same meaning as above and X is chosen from a halogen or pseudohalogen ion, in the presence of a compound of formula LnY3, or LnY3.nLiY, wherein Ln is chosen from lanthanide ions, Y is chosen from halogenide or hydroxide ions, and n is 0, 1, 2 or 3, preferably n=0, 2. According to certain embodiments, n=0.

According to certain embodiments, the reaction is carried out according to the Felkin-Anh-model, e.g. contrary to the mechanism described in J. Med. Chem., 2014, 57, pp. 4049-4057.

According to certain embodiments, Formulas II-a and II-b are represented by Formulas II-a'-1, II-b'-1, i.e. the method is a method of preparing a compound of Formula II-a'-1 or Formula II-b'-1; $R^I$ represents a linear, branched and/or cyclic alkyl or alkenyl group having 2 to 10 carbon atoms, particularly at least 3 carbon atoms for a cyclic alkyl or alkenyl group; $R^{II}$ represents methyl; $R^{III}$, $R^{IV}$ and $R^V$ have the same meanings as above; and the stereochemistry at the position marked with * is S in case the carbon atom in $R^I$ next to the carbon atom marked with * is a carbon atom with a higher priority in the Cahn Ingold Prelog system (CIP sequence rules) as the thebaine-derived ring system, e.g. a quarternary carbon atom, like e.g. in a tert-butyl group, particularly $R^I$ having at least 4 carbon atoms; or the stereochemistry at the position marked with * is R in case the carbon atom next to the carbon atom marked with * in $R^I$ is a carbon atom with a lower priority in the Cahn Ingold Prelog system as the thebaine-derived ring system, e.g. $R^I$ does not contain any quarternary or tertiary carbon atoms. According to certain embodiments, $R^I$ represents a linear, branched and/or cyclic alkyl or alkenyl group having 3 to 10 carbon atoms, particularly 3 carbon atoms, particularly an n-propyl group.

According to certain embodiments, $R^I$ represents a tert-butyl group, $R^{II}$ represents a methyl group, $R^{III}$ represents methylcyclopropyl, $R^{IV}$ represents hydrogen or methyl, particularly hydrogen, and $R^V$ represents methyl in Formula II-b'-1, the carbon-carbon bond 18,19 being a single bond, and the stereochemistry at the position marked with * is S. According to certain embodiments, $R^I$ represents an n-propyl group, $R^{II}$ represents a methyl group, $R^{III}$ represents methyl, $R^{IV}$ represents hydrogen or methyl, particularly hydrogen, and $R^V$ represents methyl in Formula II-b'-1, the carbon-carbon bond 18,19 being a single bond, and the stereochemistry at the position marked with * is R. According to certain embodiments, $R^I$ represents an n-propyl group, $R^{II}$ represents a methyl group, $R^{III}$ represents methyl, $R^{IV}$ represents hydrogen or methyl, particularly hydrogen, and $R^V$ represents methyl in Formula II-a'-1, the carbon-carbon bond 18,19 being a double bond, and the stereochemistry at the position marked with * is R.

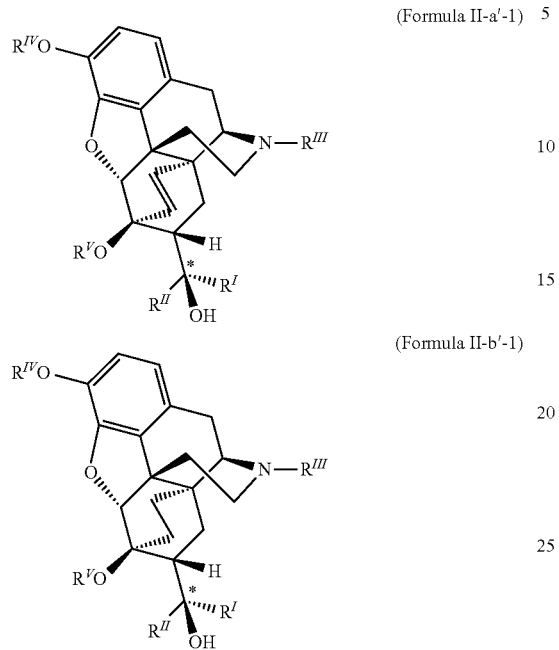

(Formula II-a'-1)

(Formula II-b'-1)

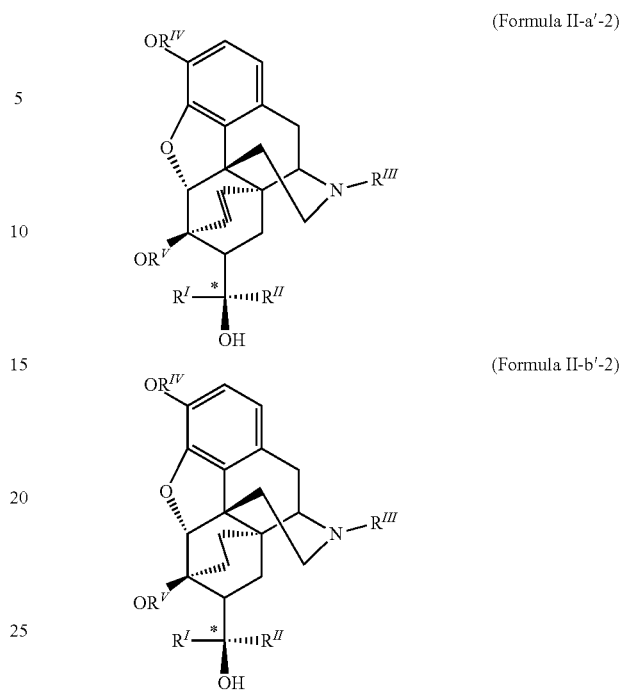

(Formula II-a'-2)

(Formula II-b'-2)

According to certain embodiments, the epimer with the S configuration at the position marked with * (the S-epimer) in case the carbon atom in $R^I$ next to the carbon atom marked with * is a carbon atom with a higher priority in the Cahn Ingold Prelog system as the thebaine-derived ring system is obtained in excess over the epimer with the R configuration at the position marked with * (the R-epimer), as e.g. shown in Formulas II-a'-2, II-b'-2, in the method of preparing a compound of Formula II-a'-1 or Formula II-b'-1 wherein $R^I$ represents a linear, branched and/or cyclic alkyl or alkenyl group having 2 to 10 carbon atoms, particularly at least 3 carbon atoms for a cyclic alkyl or alkenyl group, particularly having at least 4 carbon atoms, particularly having 4 carbon atoms, particularly a tert-butyl group; $R^{II}$ represents methyl; $R^{III}$, $R^{IV}$ and $R^V$ have the same meanings as above, particularly $R^{III}$ being methylcyclopropyl, $R^{IV}$ being hydrogen or methyl, particularly hydrogen, and $R^V$ being methyl, the carbon-carbon bond 18,19 being a single bond or double bond, particularly a single bond. That means, according to certain embodiments, a mixture of two epimers, the one mentioned above and the other epimer with the stereochemistry at the position marked with * being the opposite, i.e. R, is produced by the method, wherein the isomeric center is at the position marked with *, and the epimer described above is obtained in excess over the other epimer with the stereochemistry at the position marked with * being the opposite. According to certain embodiments, the molar ratio of S-epimer to R-epimer is at least 2:1, preferably at least 3:1, further preferably at least 4:1, even further preferably at least 5:1, particularly preferably at least 6:1, particularly in case the carbon atom in $R^I$ next to the carbon atom marked with * is a carbon atom with a higher priority in the Cahn Ingold Prelog system as the thebaine-derived ring system. In Formulas II-a'-2, II-b'-2 $R^I$ to $R^V$ have the same meaning as in Formulas II-a'-1, II-b'-1.

According to certain embodiments, the epimer with the R configuration at the position marked with * (the R-epimer) in case the carbon atom in $R^I$ next to the carbon atom marked with * is a carbon atom with a lower priority in the Cahn Ingold Prelog system as the thebaine-derived ring system is obtained in excess over the epimer with the S configuration at the position marked with * (the S-epimer), as e.g. shown in Formulas II-a'-2, II-b'-2, in the method of preparing a compound of Formula II-a'-1 or Formula II-b'-1 wherein $R^I$ represents a linear, branched and/or cyclic alkyl or alkenyl group having 2 to 10 carbon atoms, particularly at least 3 carbon atoms for a cyclic alkyl or alkenyl group, particularly having 3 carbon atoms, particularly an n-propyl group; $R^{II}$ represents methyl; $R^{III}$, $R^{IV}$ and $R^V$ have the same meanings as above, particularly $R^{III}$ being methyl, $R^{IV}$ being hydrogen or methyl, particularly hydrogen, and $R^V$ being methyl, the carbon-carbon bond 18,19 being a single bond or double bond. That means, according to certain embodiments, a mixture of two epimers, the one mentioned above and the other epimer with the stereochemistry at the position marked with * being the opposite, i.e. S, is produced by the method, wherein the isomeric center is at the position marked with *, and the epimer described above is obtained in excess over the other epimer with the stereochemistry at the position marked with * being the opposite. According to certain embodiments, the molar ratio of R-epimer to S-epimer is at least 2:1, preferably at least 3:1, further preferably at least 4:1, even further preferably at least 5:1, particularly preferably at least 6:1, particularly in case the carbon atom next to the carbon atom marked with * in $R^I$ is a carbon atom with a lower priority in the Cahn Ingold Prelog system as the thebaine-derived ring system. In Formulas II-a'-2, II-b'-2 $R^I$ to $R^V$ have the same meaning as in Formulas II-a'-1, II-b'-1.

According to certain embodiments, Formulas II-a and II-b are represented by Formulas II-a'-1, II-b'-1, i.e. the method is a method of preparing a compound of Formula II-a'-1 or Formula II-b'-1; $R^I$ represents a hydrogen or a methyl group, particularly a methyl group; $R^{II}$ represents a linear, branched and/or cyclic alkyl or alkenyl group having 2 to 10 carbon atoms, particularly at least 3 carbon atoms for a cyclic alkyl or alkenyl group; $R^{III}$, $R^{IV}$ and $R^V$ have the same meanings as above; and the stereochemistry at the position marked with * is S in case the carbon atom in $R^{II}$ next to the carbon atom marked with * is a carbon atom with a lower priority in the Cahn Ingold Prelog system (CIP sequence rules) as the thebaine-derived ring system, e.g. $R^I$ does not contain any quarternary or tertiary carbon atoms, e.g. an n-propyl group; or the stereochemistry at the position marked with * is R in case the carbon atom next to the carbon atom marked with * in $R^{II}$ is a carbon atom with a higher priority in the Cahn Ingold Prelog system as the thebaine-derived ring system, e.g. a quarternary carbon atom, like e.g. in a tert-butyl group, particularly $R^I$ having at least 4 carbon atoms. According to certain embodiments, $R^{II}$ represents a linear, branched and/or cyclic alkyl or alkenyl group having 3 to 10 carbon atoms, particularly 3 carbon atoms, particularly an n-propyl group. According to certain embodiments, $R^{II}$ represents a linear, branched and/or cyclic alkyl or alkenyl group having 3 to 10 carbon atoms, particularly 4 carbon atoms, particularly a tert-butyl group.

According to certain embodiments, $R^{II}$ represents a tert-butyl group, $R^I$ represents a methyl group, $R^{III}$ represents methylcyclopropyl, $R^{IV}$ represents hydrogen or methyl, particularly hydrogen, and $R^V$ represents methyl in Formula II-b'-1, the carbon-carbon bond 18,19 being a single bond, and the stereochemistry at the position marked with * is R. According to certain embodiments, $R^I$ represents a methyl group, $R^{II}$ represents an n-propyl group, $R^{III}$ represents methyl, $R^{IV}$ represents hydrogen or methyl, particularly hydrogen, and $R^V$ represents methyl in Formula II-b'-1, the carbon-carbon bond 18,19 being a single bond, and the stereochemistry at the position marked with * is S. According to certain embodiments, $R^I$ represents a methyl group, $R^{II}$ represents an n-propyl group, $R^{III}$ represents methyl, $R^{IV}$ represents hydrogen or methyl, particularly hydrogen, and $R^V$ represents methyl in Formula II-a'-1, the carbon-carbon bond 18,19 being a double bond, and the stereochemistry at the position marked with * is S.

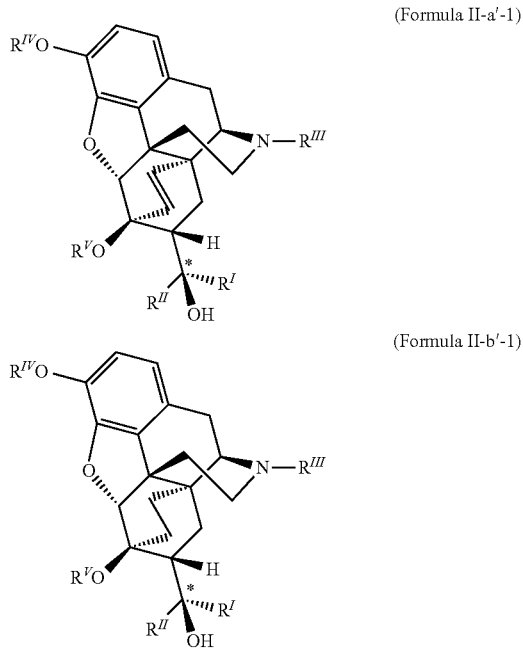

(Formula II-a'-1)

(Formula II-b'-1)

According to certain embodiments, the epimer with the R configuration at the position marked with * (the R-epimer) in case the carbon atom in $R^{II}$ next to the carbon atom marked with * is a carbon atom with a higher priority in the Cahn Ingold Prelog system as the thebaine-derived ring system is obtained in excess over the epimer with the S configuration at the position marked with * (the S-epimer), as e.g. shown in Formulas II-a'-2, II-b'-2, in the method of preparing a compound of Formula II-a'-1 or Formula II-b'-1 wherein $R^I$ represents a hydrogen or a methyl group, particularly a methyl group; $R''$ represents a linear, branched and/or cyclic alkyl or alkenyl group having 2 to 10 carbon atoms, particularly at least 3 carbon atoms for a cyclic alkyl or alkenyl group, particularly having at least 4 carbon atoms, particularly a group having 4 carbon atoms, particularly a tert-butyl group; and $R^{III}$, $R^{IV}$ and $R^V$ have the same meanings as above, particularly $R^{III}$ being methylcyclopropyl, $R^{IV}$ being hydrogen or methyl, particularly hydrogen, and $R^V$ being methyl, the carbon-carbon bond 18,19 being a single bond or a double bond. That means, according to certain embodiments, a mixture of two epimers, the one mentioned above and the other epimer with the stereochemistry at the position marked with * being the opposite, i.e. S, is produced by the method, wherein the isomeric center is at the position marked with *, and the epimer described above is obtained in excess over the other epimer with the stereochemistry at the position marked with * being the opposite. According to certain embodiments, the molar ratio of R-epimer to S-epimer is at least 2:1, preferably at least 3:1, further preferably at least 4:1, even further preferably at least 5:1, particularly preferably at least 6:1, particularly in case the carbon atom in $R^{II}$ next to the carbon atom marked with * is a carbon atom with a higher priority in the Cahn Ingold Prelog system as the thebaine-derived ring system. In Formulas II-a'-2, II-b'-2 $R^I$ to $R^V$ have the same meaning as in Formulas II-a'-1, II-b'-1.

According to certain embodiments, the epimer with the S configuration at the position marked with * (the S-epimer) in case the carbon atom in $R^{II}$ next to the carbon atom marked with * is a carbon atom with a lower priority in the Cahn Ingold Prelog system as the thebaine-derived ring system is obtained in excess over the epimer with the R configuration at the position marked with * (the R-epimer), as e.g. shown in Formulas II-a'-2, II-b'-2, in the method of preparing a compound of Formula II-a'-1 or Formula II-b'-1 wherein $R^I$ represents a hydrogen or a methyl group, particularly a methyl group; $R^{II}$ represents a linear, branched and/or cyclic alkyl or alkenyl group having 2 to 10 carbon atoms, particularly having 3 carbon atoms, particularly an n-propyl group; $R^{III}$, $R^{IV}$ and $R^V$ have the same meanings as above, particularly $R^{III}$ being methyl, $R^{IV}$ being hydrogen or methyl, particularly hydrogen, and $R^V$ being methyl, the carbon-carbon bond 18,19 being a single bond or double bond. That means, according to certain embodiments, a mixture of two epimers, the one mentioned above and the other epimer with the stereochemistry at the position marked with * being the opposite, i.e. R, is produced by the method, wherein the isomeric center is at the position marked with *, and the epimer described above is obtained in excess over the other epimer with the stereochemistry at the position marked with * being the opposite. According to certain embodiments, the molar ratio of S-epimer to R-epimer is at least 2:1, preferably at least 3:1, further preferably at least 4:1, even further preferably at least 5:1, particularly preferably at least 6:1, particularly in case the carbon atom next to the carbon atom marked with * in $R^{II}$ is a carbon atom with a lower priority in the Cahn Ingold Prelog system as the thebaine-derived ring system. In Formulas II-a'-2, II-b'-2 $R^I$ to $R^V$ have the same meaning as in Formulas II-a'-1, II-b'-1.

According to certain aspects, thus also the epimer of the compound of Formula II-a'-1 or Formula II-b'-1 is obtained, the isomeric center being at the position marked with *, and the molar ratio of the compound of Formula II-a'-1 or Formula II-b'-1 to the epimer, as e.g. shown in Formulas II-a'-2, II-b'-2, is at least 4:1, preferably at least 5:1, particularly preferably at least 6:1. In Formulas II-a'-2, II-b'-2 $R^I$ to $R^V$ have the same meaning as in Formulas II-a'-1, II-b'-1.

According to certain aspect, $R^I$ represents a linear, branched and/or cyclic alkyl or alkenyl group having 2 to 10 carbon atoms;
$R^{II}$ represents methyl;
$R^{III}$ represents hydrogen or a linear, branched and/or cyclic alkyl or alkenyl group having 1 to 10 carbon atoms or a linear, branched and/or cyclic alkoxy group having 1 to 10 carbon atoms;
$R^{IV}$ represents hydrogen or a linear, branched and/or cyclic alkyl group having 1 to 10 carbon atoms or an optionally substituted aryl or alkylaryl group having 6 to 40 carbon atom or acetyl or silyl or a protective group; and
$R^V$ represents hydrogen or a methyl group;
and the stereochemistry at the position marked with * is S in case the carbon atom in $R^I$ next to the carbon atom marked with * is a carbon atom with a higher priority in the Cahn Ingold Prelog system as the thebaine-derived ring system, or the stereochemistry at the position marked with * is R in case the carbon atom next to the carbon atom marked with * in $R^I$ is a carbon atom with a lower priority in the Cahn Ingold Prelog system as the thebaine-derived ring system in the method of preparing the compound of Formula II-a'-1 or Formula II-b'-1.

According to certain embodiments, the compounds of Formula II-a or Formula II-b, respectively Formulas II-a'-1, II-b'-1, are neither (3'S,5α,6R,7R,14α)-3'-(4,5-Epoxy-7,8-dihydro-3-hydroxy-6-methoxy-17-cyclopropylmethyl-6,14-ethano-morphinan-7-yl)-3'-(4',4'-dimethyl)pentan-3'-ol nor (3'S,5α,6R,7R,14α)-3'-(4,5-Epoxy-7,8-dihydro-3-hydroxy-6-methoxy-17-cyclopropylmethyl-6,14-etheno-morphinan-7-yl)-3'-(4',4'-dimethyl)pentan-3'-ol.

According to certain embodiments, a mixture of epimers of Formula II-a or Formula II-b, respectively Formulas II-a'-1, II-b'-1, is produced by the present method. According to certain embodiments, the epimeric excess of one epimer produced, respectively obtained by the present method to the other is at least 2:1, preferably at least 3:1, further preferably at least 4:1, even further preferably at least 5:1, particularly preferably at least 6:1, based on a molar ratio.

According to certain embodiments, the reaction is carried out in the presence of a compound of formula of formula LnY3.nLiY, wherein n is 0, 1, 2 or 3, preferably n=0, 2, in a reaction with $R^{II}$MgX, or the reaction is carried out in the presence of a compound of formula LnY3 in a reaction with $R^{II}$Li. According to certain embodiments, the reagent chosen from $R^{II}$MgX and $R^{II}$Li is $R^{II}$Li.

In this regard, a pseudohalogen ion/pseudohalide is an ion that behaves in a chemical reaction similar to a halogen group and is not particularly limited. For example, the pseudohalogen ion can be chosen from cyanide, cyanate, isocyanate, thiocyanate, isothiocyanate, selenocyanate, and azide.

In Formulas I-a, I-b, II-a' and II-b', respectively Formulas II-a'-1, II-b'-1, $R^I$, $R^{II}$, $R^{III}$, $R^{IV}$, and $R^V$ can be the same or different, provided $R^I$ and $R^{II}$ are different.

According to certain embodiments, $R^I$ represents hydrogen or a linear, branched and/or cyclic alkyl or alkenyl group having 1 to 10 carbon atoms, particularly at least 2 carbon atoms for an alkenyl group and/or at least 3 carbon atoms for a cyclic alkyl or alkenyl group, preferably a linear, branched and/or cyclic alkyl or alkenyl group having 1 to 7 carbon atoms, further preferably a linear, branched and/or cyclic alkyl group having 1 to 7 carbon atoms, particularly preferably a methyl group, a tert-butyl group or a n-propyl group, especially a tert-butyl group or a methyl group.

According to certain embodiments, $R^{II}$ represents a linear, branched and/or cyclic alkyl or alkenyl group having 1 to 10 carbon atoms, preferably a linear, branched and/or cyclic alkyl or alkenyl group having 1 to 7 carbon atoms, particularly at least 2 carbon atoms for an alkenyl group and/or at least 3 carbon atoms for a cyclic alkyl or alkenyl group, further preferably a linear, branched and/or cyclic alkyl group having 1 to 7 carbon atoms, particularly preferably a methyl group, a tert-butyl group or a n-propyl group, especially a methyl group or a n-propyl group. According to certain embodiments, a group having 1 to 10 carbon atoms, particularly at least 2 carbon atoms for an alkenyl group and/or at least 3 carbon atoms for a cyclic alkyl or alkenyl group, further preferably 1 to 7 carbon atoms as well as alkyl or alkenyl groups having a ring structure can be used as $R^{II}$. In case the alkyl or alkenyl group contains a ring the ring may have e.g. 3 to 7 carbon atoms.

According to certain embodiments, the group $R^{III}$ is a linear, branched and/or cyclic alkyl or alkenyl group having 1 to 10 carbon atoms, particularly at least 2 carbon atoms for an alkenyl group and/or at least 3 carbon atoms for a cyclic alkyl or alkenyl group, preferably a linear, branched and/or cyclic alkyl group having 1 to 10 carbon atoms, e.g. a methyl group. In embodiments wherein $R^{III}$ contains a cyclic group, e.g. an alkyl cycloalkyl or an alkenyl cycloalkyl group, $R^{III}$ has preferably 3 to 10 carbon atoms, further preferably 3 to 7 carbon atoms, more preferably 3 to 5 carbon atoms. A suitable and preferred example is e.g. a methylcyclopropyl group. Another preferred group $R^{III}$ according to certain embodiments is a methyl group.

According to certain embodiments $R^{III}$ as defined above can further be converted into a $R^{IIIb}$ being different from $R^{III}$ by nucleophilic substitution as known in the art, wherein $R^{IIIb}$ can be a linear, branched and/or cyclic alkyl or alkenyl group having 1 to 10 carbon atoms, e.g. a methyl group as well.

According to certain embodiments, the group $R^{IV}$ represents hydrogen or a linear, branched and/or cyclic alkyl group having 1 to 10 carbon atoms, particularly at least 2 carbon atoms for an alkenyl group and/or at least 3 carbon atoms for a cyclic alkyl or alkenyl group, or an optionally substituted aryl or alkylaryl group having 6 to 40 carbon atoms or acetyl or silyl or a protective group. Preferred alkylaryl groups have 6 to 25 carbon atoms, further preferably 6 to 20 carbon atoms, particularly preferably 6 to 19 carbon atoms. With regard to the optional substituents of the aryl of alkylaryl groups, these can be suitably chosen based on the target compound and can include one or more chosen from linear, branched and/or cyclic alkyl groups with one to 1 to 10 carbon atoms that can be substituted with halogen atoms and/or hydroxy groups, halogen atoms and hydroxy groups, as well as mixtures thereof. According to preferred embodiments, $R^{IV}$ represents hydrogen or a linear, branched and/or cyclic alkyl group having 1 to 10 carbon atoms, particularly at least 2 carbon atoms for an alkenyl group and/or at least 3 carbon atoms for a cyclic alkyl or alkenyl group, or an aryl or alkylaryl group having 6 to 20 carbon atoms, preferably 6 to 19 carbon atoms, or a protective group. According to further preferred embodiments, $R^{IV}$ represents hydrogen or a linear, branched and/or cyclic alkyl group having 1 to 6 carbon atoms, particularly at least 2 carbon atoms for an alkenyl group and/or at least 3 carbon atoms for a cyclic alkyl or alkenyl group, or an aryl or alkylaryl group having 6 to 19 carbon atoms, e.g. a triphenylmethyl (trityl) group, or a protective group, particularly preferably hydrogen, methyl, ethyl, phenyl, benzyl, acetyl, silyl, MOM, MEM, SEM or another protective group.

According to certain embodiments $R^{IV}$ as defined above can further by converted into a $R^{IVb}$ being different from $R^{IV}$ by a substitution reaction known in the art, wherein $R^{IVb}$ represents hydrogen or a linear, branched and/or cyclic alkyl group having 1 to 10 carbon atoms or an optionally substituted aryl or alkylaryl group having 6 to 40 carbon atoms or a protective group.

According to certain embodiments $R^{IV}$ as defined above can prior the organometallic reaction be replaced by a protective group $R^{IVa}$ which in turn can further be converted into a group $R^{IVb}$ or back into $R^{IV}$ after performing the addition by a substitution reactions known in the art.

Protective groups $R^{IVa}$ and $R^{IVb}$ can be chosen form available and suitable groups, e.g. from carbon acid esters, alkyl, allyl, silyl ethers, acetyl, benzoyl, p-methoxybenzyl, benzyl, benzyloxymethyl, tetrahydrofuran, triphenylmethyl, tetrahydropyranyl, without being limited thereto.

According to certain embodiments, $R^V$ is hydrogen or a methyl group. According to certain embodiments, $R^V$ is a methyl group.

According to certain embodiments, $R^I$ represents methyl, $R^{II}$ represents tert-butyl, $R^{III}$ represents methylcyclopropyl, $R^{IV}$ represents hydrogen or methyl, and $R^V$ represents methyl in Formula II-b', the carbon-carbon bond 18,19 being a single bond.

According to certain embodiments, $R^I$ represents methyl, $R^{II}$ represents n-propyl, $R^{III}$ represents methyl, $R^{IV}$ represents hydrogen or methyl, and $R^V$ represents methyl in Formula II-a' or Formula II-b', with carbon-carbon bond 18,19 being a single bond or a double bond.

According to certain embodiments, $R^I$ represents tert-butyl, $R^{II}$ represents methyl, $R^{III}$ represents methylcyclopropyl, $R^{IV}$ represents hydrogen or methyl, and $R^V$ represents methyl in Formula II-b', the carbon-carbon bond 18,19 being a single bond.

According to certain embodiments, $R^I$ represents n-propyl, $R^{II}$ represents methyl, $R^{III}$ represents methyl, $R^{IV}$ represents hydrogen or methyl, and $R^V$ represents methyl in Formula II-a' or Formula II-b', with carbon-carbon bond 18,19 being a single bond or a double bond.

According to certain embodiments, the compound of Formula II-b' respectively Formula II-b'-1, is S-buprenorphine. According to certain embodiments, the compound of Formula II-a' respectively Formula II-a'-1, is R-dihydroetorphine or R-etorphine, e.g. R-dihydroetorphine.

In the present method, the lanthanide ion is not particularly limited as long as it is a trivalent ion. According to certain embodiments, Ln is chosen from La, Ce and Nd ions, for which improved results can be obtained. Preferred lanthanide salts are lanthanide (III) salts like LaY3, CeY3, NdY3, or LaY3.nLiY, CeY3.nLiY, or NdY3.nLiY wherein halide ions as fluoride, chloride, bromide and iodide ions, or hydroxide ions are the preferred counter ions as Y, and n represents 0, 1, 2 or 3, preferably 0 or 2. Also mixes of the counter ions are possible in the lanthanide salts.

According to certain embodiments, the molar ratio of the compound of Formula I-a or Formula I-b to the compound of formula LnY3.nLiY in the reaction is within a range of 2:1 to 1:2, preferably within a range of 1.5:1 to 1:1.5, further preferably within a range of 1.3:1 to 1:1.3. According to certain embodiments, the molar ratio of the compound of Formula I-a or Formula I-b to the compound of formula LnY3.nLiY in the reaction is within a range of 1:1.1 to 1:2, preferably 1:1.2 to 1:1.8. Further, according to certain embodiments, the molar ratio of the compound of Formula I-a or Formula I-b to the reagent chosen from $R^{II}MgX$ and $R^{II}Li$ in the reaction is within a range of 2:1 to 1:2, preferably within a range of 1.5:1 to 1:1.5, further preferably within a range of 1.2:1 to 1:1.2. According to certain embodiments, the molar ratio of the compound of Formula I-a or Formula I-b to the reagent chosen from $R^{II}MgX$ and $R^{II}Li$ in the reaction is within a range of 1:1.1 to 1:1.5, preferably 1.15:1.3.

According to certain embodiments, a linear, branched and/or a ring containing reagent $R^{II}MgX$ or $R^{II}Li$ is used for the conversion of the keto—or preferably acetyl—group in the compound of Formula I-a or Formula I-b into the hydroxyalkyl group, wherein $R^{II}$ represents a linear, branched and/or cyclic alkyl group with 1 to 10 carbon atoms, and X represents a halogen or pseudohalogen.

According to certain embodiments, the reaction is carried out with the compound of formula $R^{II}MgX$.

According to certain embodiments, the compound of formula LnY3 or the compound of formula LnY3.nLiY, wherein n is 0, 1, 2 or 3, preferably n=0, 2, is anhydrous or is dried prior to the reaction.

According to certain embodiments, the reaction is carried out at a temperature between −100 and +15° C. According to certain embodiments, the reaction is carried out for a total time of less than 2 hours.

According to certain embodiments, reacting a compound of Formula I-a or Formula I-b with a reagent chosen from $R^{II}MgX$ and $R^{II}Li$ in the presence of a compound of formula LnY3 or LnY3.nLiY is started at a temperature below room temperature, i.e. below 20° C., preferably below 10° C., further preferably below 5° C., even further preferably at 0° C. or less, particularly preferably at less than 0° C., e.g. at less than −20° C., less than −40° C., or less than −70° C. The reaction mixture can then be left standing so that it can warm up to room temperature, e.g. 20-25° C., during the course of the reaction.

According to certain embodiments, the reaction is carried out in less than 20 hours, preferably less than 15 hours.

In certain embodiments, the reaction can be carried out at a temperature between −100 and 0° C., e.g. −90 to −20° C., preferably at about −78° C. The reaction can in these embodiments be carried out for a total time of less than 2 hours, particularly at this temperature, e.g. less than 1 hour, e.g. even less than 30 minutes. A solvent for this reaction can be suitably selected and is not particularly limited. According to preferred embodiments, the solvent comprises an ether or is an ether. In certain other embodiments, the reaction can be carried out at a temperature between −100 and +15° C., e.g. −50 to +5° C., preferably −20 to 0° C. The reaction can in these embodiments be carried out for a total time of less than 2 hours, particularly at this temperature, e.g. less than 1 hour, e.g. even less than 30 minutes. A solvent for this reaction can be suitably selected and is not particularly limited. According to preferred embodiments, the solvent comprises an ether or is an ether.

According to certain embodiments, the compound of Formula I-a or Formula I-b is added to a mixture of the reagent chosen from $R^{II}MgX$ and $R^{II}Li$ and the compound of formula LnY3 or LnY3.nLiY. According to certain embodiments, the compound of Formula I-a or Formula I-b is dissolved in a polar aprotic solvent, e.g. an ether like tetrahydrofuran, dioxane, tert-butylmethylether, 2-methyl-tetrahydrofuran, dimethylether, diethylether, dimethoxyethane, dimethoxymethane or mixtures thereof, particularly THF or dioxane. According to certain embodiments, the compound of Formula I-a or Formula I-b is not dissolved in an apolar solvent like benzene or toluene. According to certain embodiments, the compound of Formula I-a or Formula I-b is dissolved in a solvent miscible with water, particularly tetrahydrofuran (THF) or dioxane.

According to certain embodiments, the reaction is carried out in a solvent comprising an ether. Further preferably the solvent comprises an ether like tetrahydrofuran, tert-butylmethylether, 2-methyl-tetrahydrofuran, dimethylether, diethylether, dimethoxyethane, dimethoxymethane or mixtures thereof. The solvent used can further comprise solvents like dioxane, or cyclopentyl-methyl-ether, which are less preferable as sole solvents, though.

In certain aspects, the solvent comprises an ether like tetrahydrofuran, tert-butylmethylether, 2-methyl-tetrahydrofuran, dimethylether, diethylether, dimethoxyethane, dimethoxymethane or mixtures thereof with a least 30 wt. %, preferably at least 40 wt. %, with regard to all solvents used. In this regard, other solvents like dioxane or cyclopentyl-methyl-ether can be contained in the solvent mixture.

According to certain embodiments, the reaction is carried out in an ether as solvent. Preferably, the reaction is carried out using essentially tetrahydrofuran, tert-butylmethylether, 2-methyl-tetrahydrofuran, dimethylether, diethylether, dimethoxyethane, dimethoxymethane or mixtures thereof as solvent. In this regard, other solvents like dioxane or cyclopentyl-methyl-ether can be contained in the solvent mixture with less than 10 wt. %, based on the total weight of all solvents used. According to certain embodiments, the reaction is carried out using essentially a polar aprotic solvent, e.g. an ether like tetrahydrofuran, dioxane, tert-butylmethylether, 2-methyl-tetrahydrofuran, dimethylether, diethylether, dimethoxyethane, dimethoxymethane or mixtures thereof.

According to certain embodiments, the 18,19 carbon-carbon bond is a double bond (Formula I-a→Formula II-a', or Formula II-a'-1), wherein the compound of Formula II-a', Formula II-a'-1, can further be hydrogenated by classical methods, like a catalytic hydrogenation, without being limited thereto.

According to certain embodiments, the 18,19 carbon-carbon bond is a single bond (Formula I-b→Formula II-b', or Formula II-b'-1) that can be obtain by hydrogenating a starting material having a double bond using classical methods, like a catalytic hydrogenation, without being limited thereto, to arrive at the compound of Formula I-b.

An exemplary general procedure for the reaction is the following: Tetrahydrofuran as exemplary solvent is added to dry LnY3, e.g. LnCl3, at room temperature, and then the temperature is lowered to a range between −80° C. and 0° C. Lithium alkyl $R^{II}Li$ or $R^{II}MgX$ is slowly added and the mixture is kept at this low temperature for about 30 minutes. A solution of the ketone of Formula I-a or Formula I-b in a solvent, e.g. tetrahydrofuran, is added and the mixture is kept at this low temperature for 2 hours. The temperature is slowly raised to room temperature. The mixture is quenched, e.g. with aqueous ammonium chloride, and the product is extracted into a suitable extraction solvent like ethyl acetate. The ethyl acetate extract is concentrated to dryness and the residue is purified by chromatography. Typically, 1 to 2 mol equivalents of ketone of Formula I-a or Formula I-b, 1 to 2 mol equivalents of LnY3 and 1 to 2 mole equivalents $R^{II}Li$ or $R^{II}MgX$ are used.

With regard to the invention, the present method of preparing a compound of Formula II-a' or Formula II-b', respectively Formulas II-a'-1, II-b'-1, can be also seen as a method of preparing a compound of Formula II, which can be converted into a pharmaceutically acceptable salt, from a compound of Formula I, as seen in the scheme below, by a reaction with a reagent chosen from $R^{II}MgX$ and $R^{II}Li$, wherein X is chosen from a halogen or pseudohalogen ion, in the presence of a compound of formula LnY3, wherein Ln is chosen from lanthanide ions and Y is chosen from halogenide or hydroxide ions, wherein $R^I$ represents hydrogen or C1 to C10 alkyl or alkenyl, whereas the alkyl or alkenyl group is linear, cyclic and/or branched, wherein $R^{II}$ represents C1 to C10 alkyl or alkenyl, whereas the alkyl or alkenyl group is linear, cyclic and/or branched, wherein $R^{III}$ represents C1 to C10 alkyl or alkenyl, whereas the alkyl or alkenyl group is linear, cyclic and/or branched or C1 to C10 alkoxy, whereas the alkyl or alkenyl group is linear, cyclic or branched, wherein $R^{IV}$ represents C1 to C10 alkyl whereas the alkyl group is linear, cyclic or an optionally substituted aryl or alkylaryl group having 6 to 40 carbon atom or acetyl or silyl a protective group, and wherein $R^V$ represents hydrogen or methyl, and wherein the carbon-carbon bond 18-19 can be a single or a double bond. $R^I$, $R^{II}$, $R^{III}$, $R^{IV}$, and $R^V$ can have the same meanings as defined above for Formulas I-a, I-b, II-a' and II-b'. In Formulas I and II, $R^I$, $R^{II}$, $R^{III}$, $R^{IV}$, and $R^V$ can be the same or different, provided $R^I$ and $R^{II}$ are different.

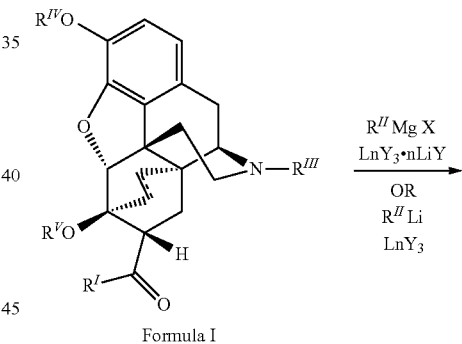

Formula I

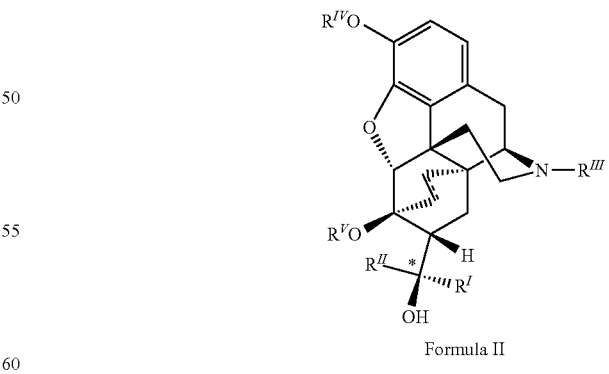

Formula II

In this regard, inventors found that stereochemistry at * in Formula II, is substantially inversed when reacting the compound of Formula I in the presence of the Lanthanide (III) salt compared to the absence of such a salt, as seen in the next reaction scheme, wherein $R^I$, $R^{II}$, $R^{III}$, $R^{IV}$, and $R^V$, Ln, X, Y and n have the same meanings as above, and which shows how exemplified stereochemistry is determined by the presence or the absence of lanthanide (III) salts. The presence or the absence of a lanthanide (III) salt determines whether conformation at * is (S) or (R).

According to certain embodiments in case the 18,19 carbon-carbon bond in Formulas I and II is a double bond that can further be hydrogenated by classical methods, as catalytic hydrogenation, without being limited thereto.

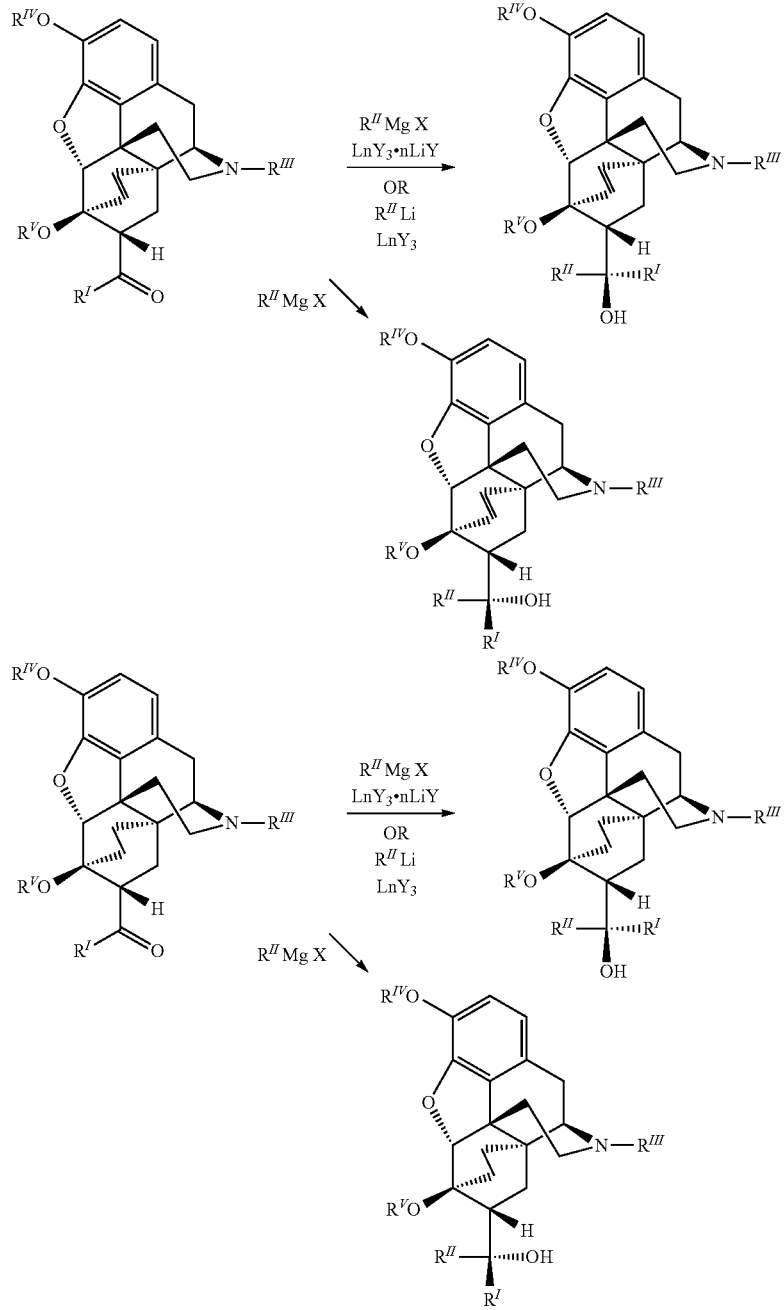

With regard to this reaction schemes, the present invention provides for a method of converting the keto group in the 7-morphine side chain in Formula I by a Grignard reaction or an organometallic reaction with alkyl-lithium to form quantitatively an alcohol having specific stereochemistry, and optionally transform the product such manufactured into an addition salt.

The inventive process gives good yield and in some cases allows a decrease in reaction steps as protection of critical groups can be avoided.

According to certain embodiments in case the 18,19 carbon-carbon bond in Formulas I and II is a single bond that can be obtain by hydrogenating the starting material of Formula I having a double bond using classical methods, as catalytic hydrogenation, without being limited thereto.

The novel process comprises the conversion of the keto group by a Grignard reaction or a reaction with alkyl-lithium to form the alcohol in the presence of a lanthanide (III) salt (Ln), preferably in the presence of a lanthanum, cerium or neodymium salt. Such obtained substance can then easily be transformed into any addition salt.

According to certain embodiments, $R^I$ represents methyl, $R^{II}$ represents tert-butyl, $R^{III}$ represents methylcyclopropyl, $R^{IV}$ represents hydrogen or methyl, and $R^V$ represents methyl in Formula II, with carbon-carbon bond 18,19 being a single bond. Thus, the R-isomer, R-epimer, at position * is obtained, i.e. R-buprenorphine or R-methylbuprenorphine.

According to certain embodiments, $R^I$ represents methyl, $R^{II}$ represents n-propyl, $R^{III}$ represents methyl, $R^{IV}$ represents hydrogen or methyl, and $R^V$ represents methyl in Formula II, with carbon-carbon bond 18,19 being a single bond or a double bond. Thus, the R-isomer, R-epimer, at position * is obtained, i.e. R-etorphine, R-methyletorphine, R-dihydroetorphine or R-dihydromethyletorphine.

According to certain embodiments, $R^I$ represents tert-butyl, $R^{II}$ represents methyl, $R^{III}$ represents methylcyclopropyl, $R^{IV}$ represents hydrogen or methyl, and $R^V$ represents methyl in Formula II-b', the carbon-carbon bond 18,19 being a single bond. Thus, the S-isomer, S-epimer, at position * is obtained, i.e. S-buprenorphine or S-methylbuprenorphine.

According to certain embodiments, $R^I$ represents n-propyl, $R^{II}$ represents methyl, $R^{III}$ represents methyl, $R^{IV}$ represents hydrogen or methyl, and $R^V$ represents methyl in Formula II-a' or Formula II-b', with carbon-carbon bond 18,19 being a single bond or a double bond. Thus, the S-isomer, S-epimer, at position * is obtained, i.e. S-etorphine, S-methyletorphine, S-dihydroetorphine or S-dihydromethyletorphine.

According to certain embodiments, the compound of Formula II, respectively Formula II-a' or Formula II-b', respectively Formulas II-a'-1, II-b'-1, is S-buprenorphine. According to certain embodiments, the compound of Formula II, respectively Formula II-a' or Formula II-b', respectively Formulas II-a'-1, II-b'-1, is R-dihydroetorphine.

The reaction can also be seen as e.g. a conversion of an acetyl group in position 7, in case $R^I$ is methyl, into a 18,19-dehydrobuprenorphine derivative/analogue having different groups $R^I$ and/or $R^{II}$ and/or $R^{III}$ and/or $R^{IV}$ and/or $R^V$ wherein $R^I$, $R^{II}$, $R^{III}$, $R^{IV}$, and $R^V$ can be the same or different, provided $R^I$ and $R^{II}$ are different, e.g. by reaction with $R^{II}$ Mg X or $R^{II}$ Li; wherein $R^I$, $R^{II}$, $R^{III}$, $R^{IV}$, and $R^V$ have the same meaning as above, and X represents a halogen or pseudohalogen ion.

In certain embodiments, the organometallic reaction can be conducted with any suitable substance to convert the acetyl group or keto group, respectively, in position 7 to an alcohol. For example, tert-butyl magnesium chloride can be used to form a desired di-methyl butanol group (e-g—a 3-(2,2-dimethylbutan-3-ol group), or n-propyl magnesium chloride is used to form the desired 2-pentanol group. Alternatively, also compounds like methyl magnesium chloride or methyllithium can be used. It is understood that all kinds of linear, branched and/or alkyl groups having a total of 1 to 10 carbon atoms, preferably 1 to 7 carbon atoms as well as alkyl groups having a ring structure can be used. In case the alkyl group contains a ring the ring may have e.g. 3 to 7 carbon atoms.

The compound of Formula II-a' or Formula II-b', respectively Formulas II-a'-1, II-b'-1, respectively the compound of Formula II, and thus also the compound of Formula I-a or I-b, can be prepared from known starting materials like oripavine or thebaine using known methods.

Oripavine or thebaine, serving as possible and preferred starting materials, can thereby be obtained from known sources. Preferably oripavine and thebaine are extracted from the latex of certain types of papaveraceae. It is also possible to use synthetic or semi-synthetic oripavine or thebaine in the present method.

In order to prepare the compound of Formula II-a' or Formula II-b', respectively Formulas II-a'-1, II-b'-1, respectively the compound of Formula II, respectively the compound of Formula I-a or I-b, for example, first the methyl group at the N-atom in position 17 of thebaine or oripavine can be suitably exchanged with a group $R^{III}$ different from methyl by e.g. nucleophilic substitution, which is not particularly limited, and can be suitably carried out as known from general synthesis methods. This nucleophilic substitution can consist of two sub-steps to replace the 17-methyl group, or generally any 17-N-alkyl group or H, by a different 17-N-alkyl or alkenyl group. First the alkyl or alkenyl group $R^I$ is introduced and then the former alkyl, e.g. methyl group, is removed. For example, a compound like oripavine or thebaine, can react with an alkyl or alkenyl $R^{III}$—X' wherein X' represents a suitable leaving group like halogenide, leading to an addition of alkyl or alkenyl, and subsequently the 17-N-methyl group or generally alkyl group or hydrogen in position 17 can be removed to e.g. obtain 17-N-alkyl nororipavine starting from oripavine.

The nucleophilic substitution can be carried out at a temperature between 0 and 100° C., e.g. 50 to 90° C., preferably 70 to 85° C., for a total time of less than 24 hours, wherein e.g. the addition step of an alkyl group can be carried out in less than 20 hours and the elimination of the alkyl, e.g. methyl, group or hydrogen in less than 4 hours. A solvent can be suitably selected for the reaction and is not particularly limited in step (i). It can be e.g. DMF (dimethylformamide) in the addition of an alkyl group and DMSO (dimethylsulfoxide) in the elimination step from the quaternary amine.

Alternatively before or after this nucleophilic substitution also the groups $R^{IV}$ and $R^V$ can optionally be introduced, depending on the target compound and starting material, by known methods. Starting from oripavine, the hydrogen in position 3 and the methyl in position 6 of the ring, or, starting from thebaine, the methyl groups in positions 3 and 6 can be suitably exchanged with groups $R^{IV}$ and $R^V$ by known methods, which are not particularly limited. Also, the exchange of groups in positions 3, 6 and 17 can be suitably carried out in any order, depending on the reactants.

Depending on the starting material and the intended compound of Formula II-a' or Formula II-b', respectively Formulas II-a'-1, II-b'-1, respectively the compound of Formula II, a substitution of the groups in position 3, 6 and/or 17 of the ring structure can be carried out or not.

Also, optionally the group in position 7 can be exchanged with different group for the following Diels-Alder-reaction.

After these optional substitutions in positions 3, 6, 7 and/or 17, the group in position 7 can be converted to the keto-group —C(CO)—$R^I$ in position 7 with the formation of the carbon-carbon double bond in positions 18, 19 using a Diels-Alder-reaction with alkylvinylketone or alkenylvinylketone or acrolein, wherein the alkyl or alkenyl or hydrogen corresponds to $R^I$, e.g. methylvinylketone. The addition of alkylvinylketone or alkenylvinylketone or acrolein can be suitably carried out using e.g. the known Diels-Alder-reaction and is not particularly limited. The addition of alkyl vinyl ketone or alkenylvinylketone or acrolein by the Diels-Alder reaction introduces an etheno group between the atoms in position 6 and 14, forming carbon-carbon bond 18,19. While adding the etheno group between the atoms in position 6 and 14, the group —C(CO)—$R^I$ is formed in position 7.

In certain embodiments, the reaction can be carried out at a temperature between 0 and 100° C., e.g. 50 to 90° C., for a total time of less than 24 hours, e.g. less than 15 hours. A solvent for the Diels-Alder-reaction can be suitably selected and is not particularly limited. Using the Diels-Alder-reaction, the R-isomer at position 7 is predominately formed. Using the Diels-Alder-reaction, a compound of Formula II-a' can for example be formed.

Of course, a compound of Formula II-a', respectively Formula II-a'-1, can also be obtained in other ways using known methods, or can be obtained by the above steps wherein some steps can be carried out in different order.

A compound of Formula II-b', respectively Formula II-b'-1, can e.g. be formed prior to the present method from a compound of Formula II-a', respectively Formula II-a'-1, by known procedures, e.g. a hydrogenation reaction, which is not particularly limited. Also, if a compound of Formula II-a', respectively Formula II-a'-1, is formed by the present method, it can be afterwards converted to a compound of Formula II-b', respectively Formula II-b'-1, by known procedures, e.g. a hydrogenation reaction, which is not particularly limited.

Such a hydrogenation reaction represents a reduction of the 18,19 etheno group bond, e.g. a reduction of the etheno group in position 18,19 to get buprenorphine or the desired analogue thereof. In certain embodiments the hydrogenation of the carbon-carbon double bound can be executed with any known technology. In certain embodiments conventional hydrogenation is indicated, in certain other embodiments the use of a hydrogen transfer agent is indicated. In the second case both an external and an internal hydrogen source can be used. Preferably this step is carried out with hydrogen gas and any appropriate catalyst. A preferred reaction system is hydrogen gas and a palladium on carbon as catalyst.

The reaction can be carried out using e.g. a hydrogenation reaction with a suitable catalyst like palladium on carbon, e.g. Pd/C with 5% Pd, or any other suitable catalyst. The pressure for the hydrogen in the hydrogenation reaction can be suitably selected and can be e.g. between 4 and 20 bar. Further, a solvent in the hydrogenation reaction can be suitably selected and can be e.g. an alcohol like methanol, ethanol, propanol like n-propanol or i-propanol, or butanol, etc. In addition, the reaction time in the hydrogenation reaction is not particularly limited, and also not the reaction temperature. A suitable reaction temperature can be e.g. between 10 and 100° C., preferably between 40 and 80° C.

The compound of Formula II-a' or Formula II-b', respectively Formulas II-a'-1, II-b'-1, respective the compound of Formula II, can be transferred into an addition salt, preferably into a pharmaceutically acceptable acid addition salts, using standard procedures as dissolving the substance in an appropriate solvent, adding the acid and crystallizing.

In certain embodiments, the preparation of the addition salt can be carried out e.g. by reacting the compound of Formula II-a' or Formula II-b', respectively Formulas II-a'-1, II-b'-1, respective the compound of Formula II, and a suitable, preferably pharmaceutical acceptable, inorganic acid like HCl, HBr, H3PO4, H2SO4, HNO3, or a suitable, preferably pharmaceutical acceptable, organic acid like maleic acid, malic acid, malonic acid, methanesulfonic acid, or 4-toluenesulfonyl acid. The solvent and reaction conditions like temperature and pressure are not particularly limited and can be suitably determined based on the compound of Formula II-a' or Formula II-b', respective the compound of Formula II, to be reacted and the acid. In certain embodiments, R-buprenorphine can be reacted with an acid to produce an R-buprenorphine salt, for example R-buprenorphine hydrochloride. The production of an R-buprenorphine salt, e.g. R-buprenorphine HCl, can be accomplished, and is not limited to, by any known reaction routes after R-buprenorphine base has been formed.

According to a further aspect, the present invention relates to a mixture of isomers, particularly epimers, of the compound of Formula II-a or Formula II-b, particularly comprising as one epimer the compound of Formula II-a'-1 or II-b'-1,

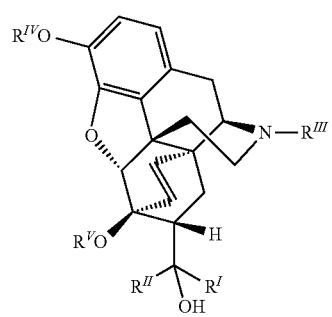

(Formula II-a)

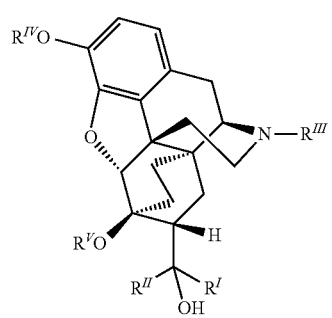

(Formula II-b)

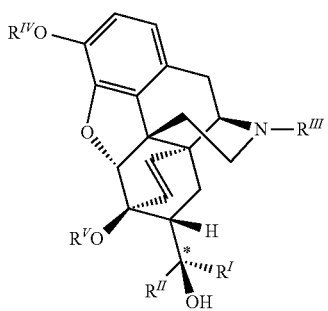

(Formula II-a'-1)

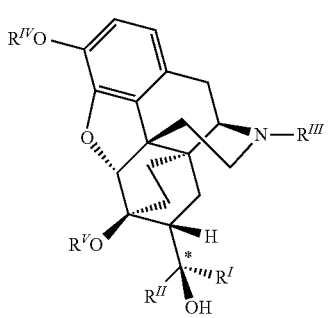

(Formula II-b'-1)

wherein $R^I$ represents hydrogen or a linear, branched and/or cyclic alkyl or alkenyl group having 1 to 10 carbon atoms; $R^{II}$ represents a linear, branched and/or cyclic alkyl or alkenyl group having 1 to 10 carbon atoms; $R^{III}$ represents hydrogen or a linear, branched and/or cyclic alkyl or alkenyl group having 1 to 10 carbon atoms or a linear, branched and/or cyclic carbonyloxyalkyl group having 1 to 10 carbon atoms or a linear, branched and/or cyclic alkoxy group having 1 to 10 carbon atoms;
$R^{IV}$ represents hydrogen or a linear, branched and/or cyclic alkyl group having 1 to 10 carbon atoms or an optionally substituted aryl or alkylaryl group having 1 to 40 carbon atom or acetyl or silyl or a protective group; and
$R^V$ represents hydrogen or a methyl group;
wherein $R^I$ and $R^{II}$ are different from each other,
which is obtained by the method of the present invention, particularly wherein the definitions for $R^I$ to $R^V$ in the compound of Formula II-a'-1 or II-b'-1 are as above described in the method of preparing them. Particularly $R^I$ to $R^V$ and the carbon-carbon bond 18,19 are as defined with regard to the method of the present invention, e.g. with regard to ratios of epimers obtained.

The isomeric center in the compounds of Formula II-a or Formula II-b, respectively Formulas II-a'-1, II-b'-1, is thereby at the carbon atom between residues $R^I$ and $R^{II}$, as already laid out with regard to the method of the present invention.

In Formulas II-a and II-b, $R^I$, $R^{II}$, $R^{III}$, $R^{IV}$, and $R^V$ can be the same or different, provided $R^I$ and $R^{II}$ are different.

According to certain embodiments, one epimer of the compound of Formula II-a or Formula II-b is represented by the compound of Formula II-a'-1 or Formula II-b'-1, respectively,

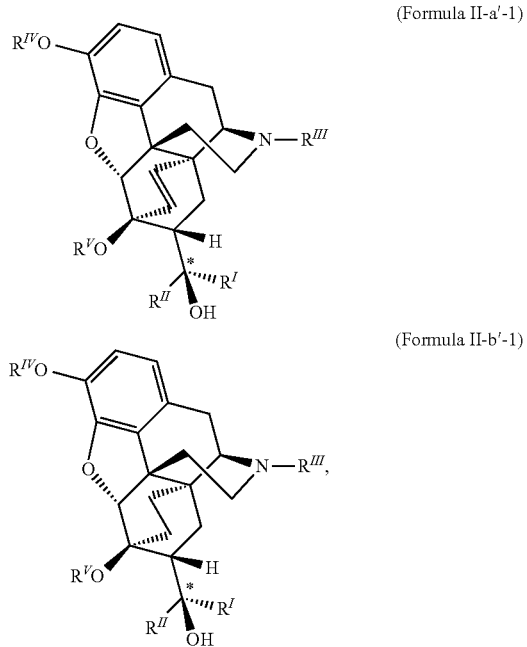

(Formula II-a'-1)

(Formula II-b'-1)

wherein $R^I$ represents a linear, branched and/or cyclic alkyl or alkenyl group having 2 to 10 carbon atoms;
$R^{II}$ represents methyl;
$R^{III}$ represents hydrogen or a linear, branched and/or cyclic alkyl or alkenyl group having 1 to 10 carbon atoms or a linear, branched and/or cyclic alkoxy group having 1 to 10 carbon atoms;
$R^{IV}$ represents hydrogen or a linear, branched and/or cyclic alkyl group having 1 to 10 carbon atoms or an optionally substituted aryl or alkylaryl group having 6 to 40 carbon atom or acetyl or silyl or a protective group; and
$R^V$ represents hydrogen or a methyl group;
and the stereochemistry at the position marked with * is S in case the carbon atom in $R^I$ next to the carbon atom marked with * is a carbon atom with a higher priority in the Cahn Ingold Prelog system as the thebaine-derived ring system, or the stereochemistry at the position marked with * is R in case the carbon atom next to the carbon atom marked with * in $R^I$ is a carbon atom with a lower priority in the Cahn Ingold Prelog system as the thebaine-derived ring system; or
wherein $R^I$ represents a hydrogen or a methyl group;
$R^{II}$ represents a linear, branched and/or cyclic alkyl or alkenyl group having 2 to 10 carbon atoms;
$R^{III}$, $R^{IV}$ and $R^V$ have the same meanings as above;
and the stereochemistry at the position marked with * is S in case the carbon atom in $R^{II}$ next to the carbon atom marked with * is a carbon atom with a lower priority in the Cahn Ingold Prelog system as the thebaine-derived ring system, or the stereochemistry at the position marked with * is R in case the carbon atom next to the carbon atom marked with * in $R^{II}$ is a carbon atom with a higher priority in the Cahn Ingold Prelog system as the thebaine-derived ring system;
and the other epimer, as e.g. shown in Formulas II-a'-2, II-b'-2 above, is determined by the isomeric center being at the position marked with *, wherein the molar ratio of the compound of Formula II-a'-1 or Formula II-b'-1 to the (other) epimer, as e.g. shown in Formulas II-a'-2, II-b'-2 above, is at least 4:1, preferably at least 5:1, particularly preferably at least 6:1. Again, in Formulas II-a'-2, II-b'-2 $R^I$ to $R^V$ have the same meaning as in Formulas II-a'-1, II-b'-1.

According to certain embodiments, $R^I$ represents a hydrogen or a methyl group;
$R^{II}$ represents a linear, branched and/or cyclic alkyl or alkenyl group having 2 to 10 carbon atoms;
$R^{III}$ represents hydrogen or a linear, branched and/or cyclic alkyl or alkenyl group having 1 to 10 carbon atoms or a linear, branched and/or cyclic alkoxy group having 1 to 10 carbon atoms;
$R^{IV}$ represents hydrogen or a linear, branched and/or cyclic alkyl group having 1 to 10 carbon atoms or an optionally substituted aryl or alkylaryl group having 6 to 40 carbon atom or acetyl or silyl or a protective group; and
$R^V$ represents hydrogen or a methyl group;
and the stereochemistry at the position marked with * is S in case the carbon atom in $R^{II}$ next to the carbon atom marked with * is a carbon atom with a lower priority in the Cahn Ingold Prelog system as the thebaine-derived ring system, or the stereochemistry at the position marked with * is R in case the carbon atom next to the carbon atom marked with * in $R^{II}$ is a carbon atom with a higher priority in the Cahn Ingold Prelog system as the thebaine-derived ring system in the compound of Formula II-a'-1 or Formula II-b'-1 in the mixture of epimers. Particularly, the molar ratio of the compound of Formula II-a'-1 or Formula II-b'-1 to the epimer, as e.g. shown in Formulas II-a'-2, II-b'-2 above, is at least 4:1, preferably at least 5:1, particularly preferably at least 6:1. In Formulas II-a'-2, II-b'-2 $R^I$ to $R^V$ have the same meaning as in Formulas II-a'-1, II-b'-1.

In the present mixture, a pharmaceutically active isomer, particularly epimer, of the compounds of Formulas II-a and II-b, e.g. of Formulas II-a'-1, II-b'-1, can be provided by the present method in excess to a pharmaceutically inactive isomer, particularly epimer, as e.g. shown in Formulas II-a'-2, II-b'-2 above, as is e.g. the case for R-buprenorphine and S-buprenorphine, and, optionally after separating the active isomer, particularly epimer, a pharmaceutical product can be produced. In Formulas II-a'-2, II-b'-2 $R^I$ to $R^V$ have the same meaning as in Formulas II-a'-1, II-b'-1.

According to certain embodiments, the present invention relates to a mixture of addition salts of the isomers, particularly epimers, of the compounds of Formula II-a or Formula II-b, particularly comprising as one epimer the compound of Formula II-a'-1 or II-b'-1. The addition salt is preferably a pharmaceutically acceptable acid addition salt and can be obtained using standard procedures as dissolving the substance in an appropriate solvent, adding the acid and crystallizing.

In certain embodiments, the acid can be a suitable, preferably pharmaceutical acceptable, inorganic acid like HCl, HBr, H3PO4, H2SO4, HNO3, or a suitable, preferably pharmaceutical acceptable, organic acid like maleic acid, malic acid, malonic acid, methanesulfonic acid, or 4-toluenesulfonyl acid.

In a further aspect the invention relates to a pharmaceutical formulation comprising a compound as represented by Formula II-a' or Formula II-b', respectively Formulas II-a'-1, II-b'-1, or a compound of Formula II, or a mixture of isomers, particularly epimers, of the compound of Formula II-a or Formula II-b, particularly comprising as one epimer the compound of Formula II-a'-1 or II-b'-1, obtained by the method according the invention.

Also, a further aspect of the invention is directed to the pharmaceutical formulation comprising a compound as represented by Formula II-a' or Formula II-b', respectively Formulas II-a'-1, II-b'-1, or a compound of Formula II, or a mixture of isomers, particularly epimers, of the compound of Formula II-a or Formula II-b, particularly comprising as one epimer the compound of Formula II-a'-1 or II-b'-1, obtained by the method according to the invention for use in a medical preparation for use in human or veterinary medicine.

Apart from comprising a compound as represented by Formula II-a' or Formula II-b', respectively Formulas II-a'-1, II-b'-1, or a compound of Formula II, or a mixture of isomers, particularly epimers, of the compound of Formula II-a or Formula II-b, particularly comprising as one epimer the compound of Formula II-a'-1 or II-b'-1, the pharmaceutical formulation is not limited. The pharmaceutical formulation of the invention can be e.g. in the form of an injection solution, a transdermal patch or for sublingual application in human and in veterinary use.

In certain embodiments, the pharmaceutical formulations for humans and/or animals of the invention further comprise one or more pharmaceutically acceptable excipients, e.g. water, stabilizers or antifungal.

These excipients are well-known to the skilled person, e.g. from Remington, The Science and Practice of Pharmacy, $22^{nd}$ Edition, 2012, which is incorporated herein by reference in regard to pharmaceutical excipients, particularly volume 1: "The Science of Pharmacy", pages 1049-1070 or from Rowe, R. C., Sheskey, P. J., Quinn, M. E., Cook, W. G., Fenton, M. E., "Handbook of Pharmaceutical Excipients", $7^{th}$ Edition, 2012, which is incorporated herein by reference in regard to pharmaceutical excipients.

According to one aspect of the invention, the pharmaceutical formulation of the present invention can be used in human and veterinary medicine. Another aspect of the invention relates to the use of the compound as represented by Formula II-a' or Formula II-b', respectively Formulas II-a'-1, II-b'-1, or a compound of Formula II, or a mixture of isomers, particularly epimers, of the compound of Formula II-a or Formula II-b, particularly comprising as one epimer the compound of Formula II-a'-1 or II-b'-1, in a pharmaceutical formulation.

In addition, the invention relates in a further aspect to the use of the compound as represented by Formula II-a' or Formula II-b', respectively Formulas II-a'-1, II-b'-1, or a compound of Formula II, or a mixture of isomers, particularly epimers, of the compound of Formula II-a or Formula II-b, particularly comprising as one epimer the compound of Formula II-a'-1 or II-b'-1, obtained by the method according the invention in a pharmaceutical formulation.

EXAMPLES

The present invention will now be described in detail with reference to several examples thereof. However, these examples are illustrative and do not limit the scope of the invention.

General Procedure

LnCl3 is dried under vacuum at a temperature at or above about 150° C. After cooling the LnCl3 to room temperature of about 22° C., tetrahydrofuran is added and the temperature is lowered to a range between −80° C. and 0° C. Lithium alkyl is added drop-wise and the mixture is kept at the low temperature for 30 minutes. A solution of the ketone in tetrahydrofuran is added and the mixture is kept at this low temperature for 2 hours.

Afterwards the temperature is raised to room temperature without external heating. After 6 or more hours the mixture is quenched with aqueous ammonium chloride and the product is extracted into ethyl acetate. The ethyl acetate extracts are concentrated to dryness and the residue is purified by column chromatography using silica as solid phase and ethyl acetate/heptane mixtures as mobile phase.

Typically 1 to 2 mole equivalents of ketone, 1 to 2 mole equivalents of LnCl3 and 1 to 2 mole equivalents alkyl-lithium are used.

In the examples, different examples of compounds of Formula I-a or Formula I-b were reacted with different reagents chosen from $R^{II}MgX$ and $R^{II}Li$ to arrive at different compounds of Formula II-a or Formula II-b, wherein typically mixtures of both isomers, particularly epimers, at the isomeric C-atom shown e.g. in Formula II-a'-1 and Formula II-b'-1 were obtained. For the different compounds, the different residues $R^I$ to $R^V$ are usually referred to, unless noted otherwise, as well as the amount of stereoisomers, particularly epimers, produced. The residues $R^I$ to $R^V$, the reagents chosen from $R^{II}MgX$ and $R^{II}Li$, and the lanthanide salt, if applied, can also be taken from Table 2. The two resulting isomers, particularly epimers, in each example and comparative example were analyzed regarding structure and content of each isomer, particularly epimer, using NMR and HPLC as follows:

Structure analysis: After a chromatographic separation, as given in the examples, the structures of the two isomers were analyzed using NMR spectroscopy (400 MHz Agilent).

Quantitative analysis: A sample of the resulting product mixture in each example with a sample volume of 10 µl and a concentration of 1 mg/ml was subjected to HPLC separation (Waters alliance LC-System/Agilent 1100,1200) with a SymmetryShield RP18; 100×4.6 mm, 3.5 mm column using 5 g ammonium acetate dissolved in 1000 ml Milli Q water as eluent A and methanol as eluent B according to the gradient given in Table 1. The resulting peaks for each isomer were measured using the software Empower for area analysis using standard procedure. The results of the area detection for each example are given in Table 2.

TABLE 1

Exemplary Gradient in HPLC separation (flow rate of 1.0 ml/min)

| Time (min) | Eluent A (%) | Eluent B (%) |
|---|---|---|
| 0 | 57 | 43 |
| 4 | 57 | 43 |
| 12 | 35 | 65 |
| 15 | 35 | 65 |
| 18 | 10 | 90 |
| 24 | 10 | 90 |
| 25 | 57 | 43 |
| 30 | 57 | 43 |

Example 1

CeCl3.7H2O (493 mg, 1.3 mmol) was dried in vacuo at 150° C. for 5 h, then cooled to 22° C. Tetrahydrofuran (4 mL) was added under nitrogen atmosphere and the mixture was cooled to −78° C. Tert-butyl lithium (76.86 mg, 1.2 mmol) in 2.0 mL pentane was added. The opiate represented by Formula 3 (497.6 mg, 1 mmol), dissolved in 2 ml tetrahydrofuran, was added at −78° C. and the mixture stirred overnight and slowly warmed to 22° C. The mixture was quenched with saturated aqueous NH4Cl solution (6 mL) and extracted twice with 6 mL ethyl acetate. The organic phase was washed with 3 mL saturated aqueous NaCl solution, dried over MgSO4 and concentrated in vacuo to yield 440 mg of the crude mixture. The crude product was purified by column chromatography using silica as solid phase and ethyl acetate/heptane mixtures as mobile phase and analyzed using NMR, as described above. Total yield was 79%, which contained 64.7% of the desired product having (R) conformation as represented by Formula 4a and 14.3% of the product having (S) conformation represented by Formula 4b, as determined using the above HPLC measurement. The procedure resulted in a final purity of 99.1% of the desired product having (R) conformation.

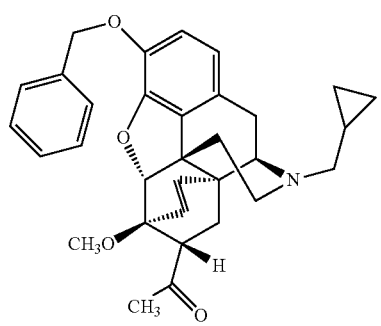

(Formula 3)

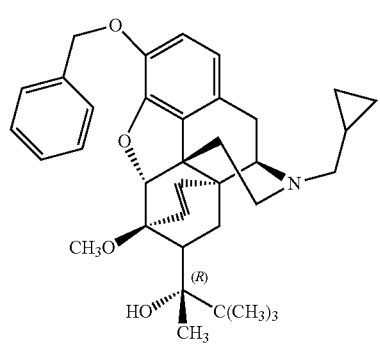

(Formula 4a)

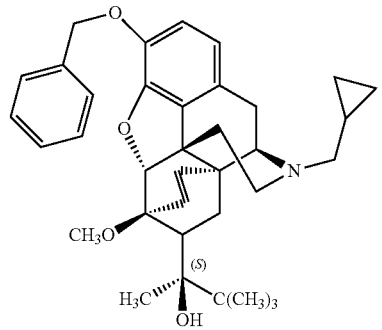

(Formula 4b)

Comparative Examples 2 to 4

Comparative examples 2 to 4 were conducted in absence of a Lanthanide (III) salt but otherwise under the same conditions and using the same molar ratios as described in example 1, with different starting compounds with different residues $R^I$, $R^{III}$, and $R^{IV}$, as described in Table 2. In all examples 2 to 4, $R^V$ was methyl. The (S) product of comparative example 2 is represented by Formula 5. In all cases yield was between 35% and 61%.

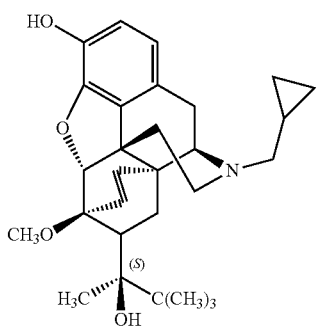

Formula 5

Examples 5 to 7

Examples according to the invention have been conducted in presence of a Lanthanide (III) salt given in Table 2 under the same conditions and using the same molar ratios as described in example 1, with different starting compounds with different residues $R^I$, $R^{III}$, and $R^{IV}$, as described in Table 2. In all examples 5 to 7, $R^V$ was methyl. In Example 6 $LiR^{II}$ was used instead of the Grignard reagent $R^{II}MgX$. In all cases yield was between 74% and 81% and the ratio of the desired product to the other isomer was about 54:12 to 83:9.

Example 7a

Example 7a according to the invention has been conducted under same conditions as examples 5 to 7 with the difference that the opiate represented by Formula 3, dissolved in tetrahydrofuran, was added at 0° C.

TABLE 2 selected residues in Examples 1 and 5 to 7 and Comparative Examples 2 to 4

| | $R^I$ | organometallic reagent: $R^{II}MgX$ or $R^{II}Li$ | $R^{III}$ | $R^{IV}$ | 18, 19 bond | Ln | Yield (%) | Ratio |
|---|---|---|---|---|---|---|---|---|
| 1 | Methyl | tert-Butyl Li | Methyl-cyclopropyl | Benzyl | Double | CeCl3 | 79 | 4.5:1.0 |
| 2 | Methyl | tert-Butyl Mg Cl | Methyl-cyclopropyl | H | Double | — | 35 | 1.0:5.8 |
| 3 | Methyl | Propyl Mg Cl | Methyl | H | Single | — | 61 | 1.0:6.5 |
| 4 | Methyl | Propyl Mg Cl | Methyl | H | Double | — | 50 | 1.0:6.6 |
| 5 | Methyl | tert-Butyl Li | Methyl-cyclopropyl | Benzyl | Double | LaCl3 | 74 | 5.1:1.0 |
| 6 | Tert-Butyl | Methyl Li | Methyl | Methyl | Single | LaCl3 | 81 | 4.7:1.0 |
| 7 | Methyl | tert-Butyl Mg Cl | Methyl-cyclopropyl | Benzyl | Double | LaCl3•2LiCl | 78 | 9.0:1.0 |
| 7a | Methyl | tert-Butyl Mg Cl | Methyl-cyclopropyl | Benzyl | Double | LaCl3•2LiCl | 78 | 8.9:1.0 |

Yield: starting material expressed as quantity of substance (molar proportion) that has been converted.
Ratio: Area-% of desired isomer following the invention to area % of undesired isomer in HPLC measurement.

A method has been shown herein for preparing stereoisomers, particularly epimers, of buprenorphine and analogues thereof, comprising but not limited to etorphine, dihydroetorphine and analogues thereof and their salts.

With the present method, it is possible to obtain substances by a short synthesis. Further, the need of using intermediates by introducing and later releasing protective groups is avoided, thus limiting efforts and costs of the present process. In addition, the present method allows for an influence of the stereochemical conformation of the resulting product. Compared to a reaction without the addition of a lanthanide salt, the present method also enables the use of a wide variety of starting materials for producing a product with desired stereochemistry.

All references cited in this specification are herewith incorporated by reference in their entirety.

The present method has been described in detail with reference to certain embodiments and specified by examples. However, a skilled person will acknowledge that also other modifications, changes, or similar alterations can be made to the present invention without deviating from the spirit of the invention.

The invention claimed is:

1. A method of preparing a compound of Formula II-a'-1 or Formula II-b'-1,

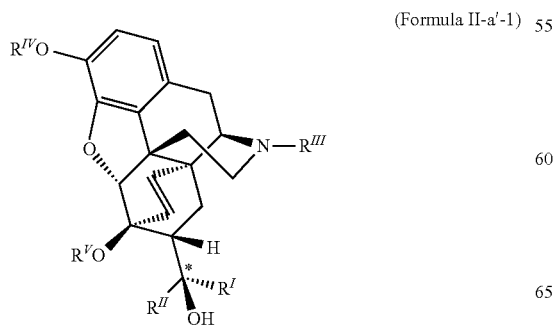

(Formula II-a'-1)

-continued

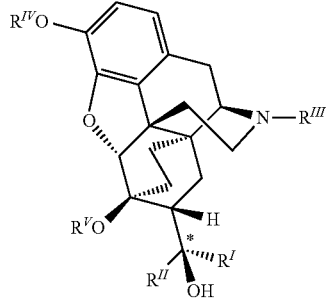

(Formula II-b'-1)

wherein $R^I$ represents a linear, branched and/or cyclic alkyl or alkenyl group having 2 to 10 carbon atoms;
$R^{II}$ represents methyl;
$R^{III}$ represents hydrogen or a linear, branched and/or cyclic alkyl or alkenyl group having 1 to 10 carbon atoms or a linear, branched and/or cyclic alkoxy group having 1 to 10 carbon atoms;
$R^{IV}$ represents a linear, branched and/or cyclic alkyl group having 1 to 10 carbon atoms or an optionally substituted aryl or alkylaryl group having 6 to 40 carbon atom or acetyl or silyl or a protective group; and
$R^V$ represents hydrogen or a methyl group;
and the stereochemistry at the position marked with * is S in case the carbon atom in $R^I$ next to the carbon atom marked with * is a carbon atom with a higher priority in the Cahn Ingold Prelog system as the thebaine-derived ring system, or the stereochemistry at the position marked with * is R in case the carbon atom next to the carbon atom marked with * in $R^I$ is a carbon atom with a lower priority in the Cahn Ingold Prelog system as the thebaine-derived ring system; or
wherein $R^I$ represents a hydrogen or a methyl group;
$R^{II}$ represents a linear, branched and/or cyclic alkyl or alkenyl group having 2 to 10 carbon atoms;
$R^{III}$, $R^{IV}$ and $R^V$ have the same meanings as above;
and the stereochemistry at the position marked with * is S in case the carbon atom in $R^{II}$ next to the carbon atom marked with * is a carbon atom with a lower priority in the Cahn Ingold Prelog system as the thebaine-derived ring system, or the stereochemistry at the position marked with * is R in case the carbon atom next to the carbon atom marked with * in $R^{II}$ is a carbon atom with a higher priority in the Cahn Ingold Prelog system as the thebaine-derived ring system,
involving:
reacting a compound of Formula I-a or Formula I-b

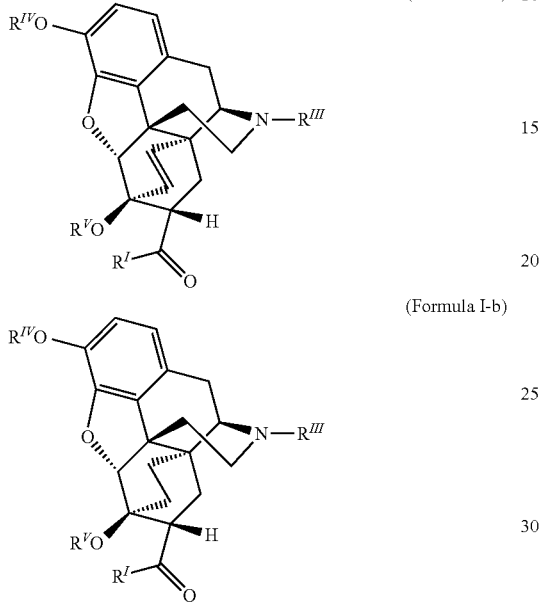

(Formula I-a)

(Formula I-b)

wherein $R^{I}$, $R^{III}$, $R^{IV}$ and $R^{V}$ have the same meanings as above,
with a reagent chosen from $R^{II}MgX$ and $R^{II}Li$, wherein $R^{II}$ has the same meaning as above and X is chosen from a halogen or pseudohalogen ion, in the presence of a compound of formula $LnY3.nLiY$, wherein Ln is chosen from lanthanide ions and Y is chosen from halogenide or hydroxide ions, and n is 0, 1, 2 or 3, preferably n=0, 2.

2. The method of claim 1, wherein also the epimer of the compound of Formula II-a'-1 or Formula II-b'-1 is obtained, the isomeric center being at the position marked with *, and the molar ratio of the compound of Formula II-a'-1 or Formula II-b'-1 to the epimer is at least 4:1.

3. The method of claim 1, wherein $R^{I}$ represents a linear, branched and/or cyclic alkyl or alkenyl group having 2 to 10 carbon atoms;
$R^{II}$ represents methyl;
$R^{III}$ represents hydrogen or a linear, branched and/or cyclic alkyl or alkenyl group having 1 to 10 carbon atoms or a linear, branched and/or cyclic alkoxy group having 1 to 10 carbon atoms;
$R^{IV}$ represents a linear, branched and/or cyclic alkyl group having 1 to 10 carbon atoms or an optionally substituted aryl or alkylaryl group having 6 to 40 carbon atom or acetyl or silyl or a protective group; and
$R^{V}$ represents hydrogen or a methyl group;
and the stereochemistry at the position marked with * is S in case the carbon atom in $R^{I}$ next to the carbon atom marked with * is a carbon atom with a higher priority in the Cahn Ingold Prelog system as the thebaine-derived ring system, or the stereochemistry at the position marked with * is R in case the carbon atom next to the carbon atom marked with * in $R^{I}$ is a carbon atom with a lower priority in the Cahn Ingold Prelog system as the thebaine-derived ring system.

4. A method of preparing a compound of Formula II-a' or Formula II-b',

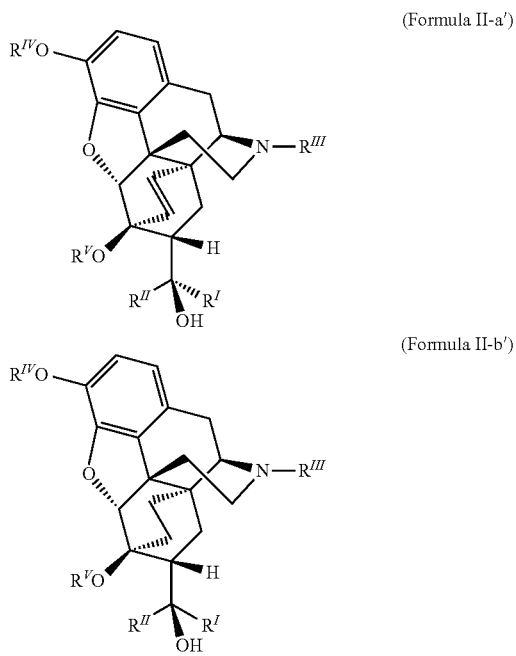

(Formula II-a')

(Formula II-b')

wherein $R^{I}$ represents hydrogen or a linear, branched and/or cyclic alkyl or alkenyl group having 1 to 10 carbon atoms;
$R^{II}$ represents a linear, branched and/or cyclic alkyl or alkenyl group having 1 to 10 carbon atoms;
$R^{III}$ represents hydrogen or a linear, branched and/or cyclic alkyl or alkenyl group having 1 to 10 carbon atoms or a linear, branched and/or cyclic alkoxy group having 1 to 10 carbon atoms;
$R^{IV}$ represents a linear, branched and/or cyclic alkyl group having 1 to 10 carbon atoms or an optionally substituted aryl or alkylaryl group having 6 to 40 carbon atom or acetyl or silyl or a protective group; and
$R^{V}$ represents hydrogen or a methyl group;
wherein $R^{I}$ and $R^{II}$ are different from each other,
involving:
reacting a compound of Formula I-a or Formula I-b

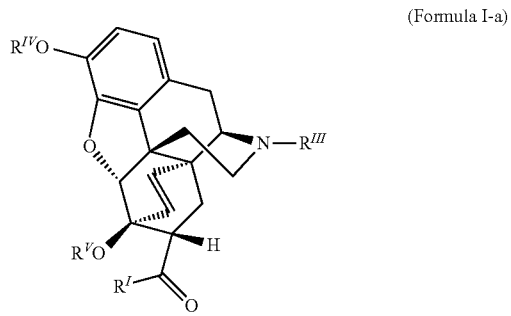

(Formula I-a)

-continued

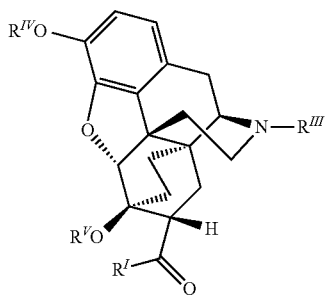

(Formula I-b)

wherein $R^I$, $R^{III}$, $R^{IV}$ and $R^V$ have the same meanings as above, with a reagent chosen from $R^{II}MgX$ and $R^{II}Li$, wherein $R^{II}$ has the same meaning as above and X is chosen from a halogen or pseudohalogen ion, in the presence of a compound of formula $LnY3.nLiY$, wherein Ln is chosen from lanthanide ions and Y is chosen from halogenide or hydroxide ions, and n is 0, 1, 2 or 3, preferably n=0, 2.

5. The method of claim 1, wherein Ln is chosen from La, Ce and Nd ions.

6. The method of claim 1, wherein the molar ratio of the compound of Formula I-a or Formula I-b to the compound of formula $LnY3.nLiY$ is within a range of 2:1 to 1:2.

7. The method of claim 1, wherein the reaction is carried out with the compound of formula $R^{II}MgX$.

8. The method of claim 1, wherein the compound of formula $LnY3.nLiY$ is anhydrous or is dried prior to the reaction.

9. The method of claim 1, wherein the reaction is carried out at a temperature between −100 and +15° C.

10. The method of claim 1, wherein the reaction is carried out for a total time of less than 2 hours.

11. The method of claim 1, wherein the reaction is carried out in a solvent comprising an ether.

12. The method of claim 1, wherein the reaction is carried out in an ether as solvent.

13. A mixture of epimers of the compound of Formula II-a or Formula II-b,

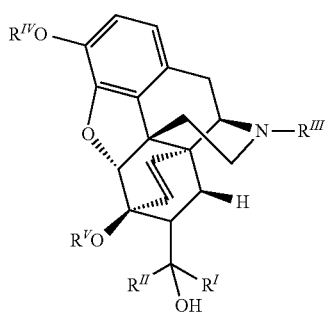

(Formula II-a)

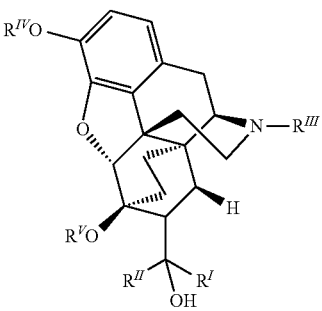

(Formula II-b)

wherein $R^I$ represents hydrogen or a linear, branched and/or cyclic alkyl or alkenyl group having 1 to 10 carbon atoms;

$R^{II}$ represents a linear, branched and/or cyclic alkyl or alkenyl group having 1 to 10 carbon atoms;

$R^{III}$ represents hydrogen or a linear, branched and/or cyclic alkyl or alkenyl group having 1 to 10 carbon atoms or a linear, branched and/or cyclic carbonyloxy-alkyl group having 1 to 10 carbon atoms or a linear, branched and/or cyclic alkoxy group having 1 to 10 carbon atoms;

$R^{IV}$ represents a linear, branched and/or cyclic alkyl group having 6 to 10 carbon atoms or an optionally substituted aryl or alkylaryl group having 6 to 40 carbon atom or acetyl or silyl or a protective group; and $R^V$ represents hydrogen or a methyl group;

wherein $R^I$ and $R^{II}$ are different from each other, which is obtained by a method of claim 4.

14. The mixture of epimers of claim 13, wherein one epimer of the compound of Formula II-a or Formula II-b is represented by the compound of Formula II-a'-1 or Formula II-b'-1, respectively,

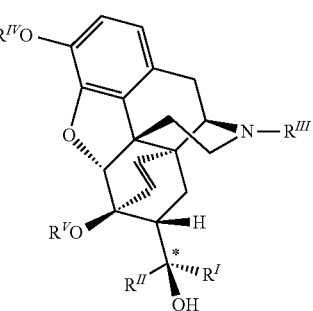

(Formula II-a'-1)

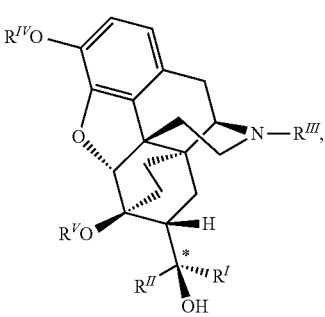

(Formula II-b'-1)

wherein $R^I$ represents a linear, branched and/or cyclic alkyl or alkenyl group having 2 to 10 carbon atoms;

$R^{II}$ represents methyl;

$R^{III}$ represents hydrogen or a linear, branched and/or cyclic alkyl or alkenyl group having 1 to 10 carbon atoms or a linear, branched and/or cyclic alkoxy group having 1 to 10 carbon atoms;

$R^{IV}$ represents a linear, branched and/or cyclic alkyl group having 6 to 10 carbon atoms or an optionally substituted aryl or alkylaryl group having 6 to 40 carbon atom or acetyl or silyl or a protective group; and $R^{V}$ represents hydrogen or a methyl group;

and the stereochemistry at the position marked with * is S in case the carbon atom in $R^{I}$ next to the carbon atom marked with * is a carbon atom with a higher priority in the Cahn Ingold Prelog system as the thebaine-derived ring system, or the stereochemistry at the position marked with * is R in case the carbon atom next to the carbon atom marked with * in $R^{I}$ is a carbon atom with a lower priority in the Cahn Ingold Prelog system as the thebaine-derived ring system; or wherein $R^{I}$ represents a hydrogen or a methyl group;

$R^{II}$ represents a linear, branched and/or cyclic alkyl or alkenyl group having 2 to 10 carbon atoms;

$R^{III}$, $R^{IV}$ and $R^{V}$ have the same meanings as above;

and the stereochemistry at the position marked with * is S in case the carbon atom in $R^{II}$ next to the carbon atom marked with * is a carbon atom with a lower priority in the Cahn Ingold Prelog system as the thebaine-derived ring system, or the stereochemistry at the position marked with * is R in case the carbon atom next to the carbon atom marked with * in $R^{II}$ is a carbon atom with a higher priority in the Cahn Ingold Prelog system as the thebaine-derived ring system;

and the other epimer is determined by the isomeric center being at the position marked with *, wherein the molar ratio of the compound of Formula II-a'-1 or Formula II-b'-1 to the epimer is at least 4:1.

15. The mixture of epimers of claim 14, wherein in the compound of Formula II-a'-1 or Formula II-b'-1 $R^{I}$ represents a hydrogen or a methyl group;

$R^{II}$ represents a linear, branched and/or cyclic alkyl or alkenyl group having 2 to 10 carbon atoms;

$R^{III}$ represents hydrogen or a linear, branched and/or cyclic alkyl or alkenyl group having 1 to 10 carbon atoms or a linear, branched and/or cyclic alkoxy group having 1 to 10 carbon atoms;

$R^{IV}$ represents a linear, branched and/or cyclic alkyl group having 6 to 10 carbon atoms or an optionally substituted aryl or alkylaryl group having 6 to 40 carbon atom or acetyl or silyl or a protective group; and $R^{V}$ represents hydrogen or a methyl group;

and the stereochemistry at the position marked with * is S in case the carbon atom in $R^{II}$ next to the carbon atom marked with * is a carbon atom with a lower priority in the Cahn Ingold Prelog system as the thebaine-derived ring system, or the stereochemistry at the position marked with * is R in case the carbon atom next to the carbon atom marked with * in $R^{II}$ is a carbon atom with a higher priority in the Cahn Ingold Prelog system as the thebaine-derived ring system.

* * * * *